(12) United States Patent
Dinsmore et al.

(10) Patent No.: US 6,387,903 B1
(45) Date of Patent: May 14, 2002

(54) INHIBITORS OF PRENYL-PROTEIN TRANSFERASE

(75) Inventors: Christopher J Dinsmore, Schwenksville; John H. Hutchinson, Philadelphia; Theresa M. Williams, Harleysville, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/463,917

(22) Filed: Feb. 1, 2000

Related U.S. Application Data

(60) Provisional application No. 60/057,080, filed on Aug. 27, 1997.

(51) Int. Cl.[7] .................... C07D 403/06; A61K 31/496
(52) U.S. Cl. ...................................... 514/252; 544/370
(58) Field of Search ......................... 544/370; 514/252

(56) References Cited

U.S. PATENT DOCUMENTS

| | | | |
|---|---|---|---|
| 5,736,539 A | | 4/1998 | Graham et al. |
| 5,856,326 A | | 1/1999 | Anthony |
| 5,972,942 A | * | 10/1999 | Wei ............................ 514/252 |

FOREIGN PATENT DOCUMENTS

| | | |
|---|---|---|
| JP | 48-28679 | 3/1973 |
| JP | H7-112930 | 10/1993 |
| WO | WO95/08542 | 9/1993 |
| WO | WO 95/00497 | 1/1995 |
| WO | WO96/30343 | 10/1996 |
| WO | WO97/36593 | 10/1997 |

OTHER PUBLICATIONS

J. of Biol. Chem., vol. 270, No. 45 pp. 26770–26773 (1995), by E. C. Lerner, et al.

Cancer Research, vol. 57, pp. 1846–1850 (1997), by K. Miquel, et al.

J. of Biol. Chem., vol. 266, No. 22, p. 14603–14610 (1991), by S. L. Moores, et al.

Bioorganic & Medicinal Chem., vol. 4, No. 9, pp. 1537–1543 (1996), by J. D. Scholten, et al.

Nature Medicine, vol. 1, No. 8, pp. 792–797 (1995), by N. E. Kohl, et al.

Proc. Natl. Acad. Sci. USA. vol. 91, pp. 9141–91445 (1994), by N. E. Kohl, et al.

J. of Biol. Chem., 270, No. 11, pp. 6221–6226 (1995, by G. L. James, et al.

Cancer Research, vol., 55, pp. 3295–3304 (1995), by M. B. Dalton, et al.

Exp. Opin. Ther. Patents, vol. 5, No. 12, pp. 1269–1285 (1995), by S. L. Graham.

Cancer Research, vol. 55, pp. 5302–5309 (1995), L. Sepp–Lorenzino, et al.

J. of Med. Chem., vol. 7, No. 2, pp. 154–158 (1964) by O. E. Fanceher, et al.

* cited by examiner

*Primary Examiner*—Robert Gerstl
(74) *Attorney, Agent, or Firm*—J. Antonio Garcia-Rivas; Mark R. Daniel

(57) ABSTRACT

The present invention is directed to compounds which inhibit prenyl-protein transferases, farnesyl-protein transferase and geranylgeranyl-protein transferase type I, and the prenylation of the oncogene protein Ras. The invention is further directed to chemotherapeutic compositions containing the compounds of this invention and methods for inhibiting farnesyl-protein transferase and geranylgeranyl-protein transferase type I and the prenylation of the oncogene protein RAS.

12 Claims, No Drawings

SEQUENCE LISTING

<160> NUMBER OF SEQ ID NOS: 21

<210> SEQ ID NO 1
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 1

Cys Val Leu Ser
 1

<210> SEQ ID NO 2
<211> LENGTH: 15
<212> TYPE: PRT
<213> ORGANISM: Artificial Sequence
<220> FEATURE:
<223> OTHER INFORMATION: synthesized peptide subst rate for
      geranylgeranyl-prtoein transferase type I

<400> SEQUENCE: 2

Gly Lys Lys Lys Lys Lys Lys Ser Lys Thr L ys Cys Val Ile Met
 1               5                  10                  15

<210> SEQ ID NO 3
<211> LENGTH: 52
<212> TYPE: DNA
<213> ORGANISM: Artificial Sequence
<220> FEATURE:
<223> OTHER INFORMATION: completely synthesized nu cleotide sequence

<400> SEQUENCE: 3
gagagggaat tcgggcccttt cctgcatgct gctgctgctg ctgctgctgg g c            52

<210> SEQ ID NO 4
<211> LENGTH: 41
<212> TYPE: DNA
<213> ORGANISM: Artificial Sequence
<220> FEATURE:
<223> OTHER INFORMATION: completely synthesized nu cleotide sequence

<400> SEQUENCE: 4
gagagagctc gaggttaacc cgggtgcgcg gcgtcggtgg t                         41

<210> SEQ ID NO 5
<211> LENGTH: 42
<212> TYPE: DNA
<213> ORGANISM: Artificial Sequence
<220> FEATURE:
<223> OTHER INFORMATION: completely synthesized nu cleotide sequence

<400> SEQUENCE: 5
gagagagtct agagttaacc cgtggtcccc gcgttgcttc ct                        42

<210> SEQ ID NO 6
<211> LENGTH: 43
<212> TYPE: DNA
<213> ORGANISM: Artificial Sequence
<220> FEATURE:
<223> OTHER INFORMATION: completely synthesized nu cleotide sequence

<400> SEQUENCE: 6
gaagaggaag cttggtaccg ccactgggct gtaggtggtg gct                       43

<210> SEQ ID NO 7
<211> LENGTH: 27
<212> TYPE: DNA
<213> ORGANISM: Artificial Sequence
<220> FEATURE:
<223> OTHER INFORMATION: completely synthesized nu cleotide sequence

<400> SEQUENCE: 7
ggcagagctc gtttagtgaa ccgtcag                27

<210> SEQ ID NO 8
<211> LENGTH: 27
<212> TYPE: DNA
<213> ORGANISM: Artificial Sequence
<220> FEATURE:
<223> OTHER INFORMATION: completely synthesized nu cleotide sequence

<400> SEQUENCE: 8
gagagatctc aaggacggtg actgcag                27

<210> SEQ ID NO 9
<211> LENGTH: 86
<212> TYPE: DNA
<213> ORGANISM: Artificial Sequence
<220> FEATURE:
<223> OTHER INFORMATION: completely synthesized nu cleotide sequence

<400> SEQUENCE: 9
tctcctcgag gccaccatgg ggagtagcaa gagcaagcct aaggacccca g ccagcgccg    60 gatgacagaa tacaagcttg tggtgg                86

<210> SEQ ID NO 10
<211> LENGTH: 33
<212> TYPE: DNA
<213> ORGANISM: Artificial Sequence
<220> FEATURE:
<223> OTHER INFORMATION: completely synthesized nu cleotide sequence

<400> SEQUENCE: 10
cacatctaga tcaggacagc acagacttgc agc           33

<210> SEQ ID NO 11
<211> LENGTH: 41
<212> TYPE: DNA
<213> ORGANISM: Artificial Sequence
<220> FEATURE:
<223> OTHER INFORMATION: completely synthesized nu cleotide sequence

<400> SEQUENCE: 11
tctcctcgag gccaccatga cagaatacaa gcttgtggtg g       41

<210> SEQ ID NO 12
<211> LENGTH: 38
<212> TYPE: DNA
<213> ORGANISM: Artificial Sequence
<220> FEATURE:
<223> OTHER INFORMATION: completely synthesized nu cleotide sequence

<400> SEQUENCE: 12
cactctagac tggtgtcaga gcagcacaca cttgcagc         38

<210> SEQ ID NO 13
<211> LENGTH: 38
<212> TYPE: DNA

```
<213> ORGANISM: Artificial Sequence
<220> FEATURE:
<223> OTHER INFORMATION: completely synthesized nu cleotide sequence

<400> SEQUENCE: 13
gagagaattc gccaccatga cggaatataa gctggtgg                              38

<210> SEQ ID NO 14
<211> LENGTH: 33
<212> TYPE: DNA
<213> ORGANISM: Artificial Sequence
<220> FEATURE:
<223> OTHER INFORMATION: completely synthesized nu cleotide sequence

<400> SEQUENCE: 14
gagagtcgac gcgtcaggag agcacacact tgc                                   33

<210> SEQ ID NO 15
<211> LENGTH: 22
<212> TYPE: DNA
<213> ORGANISM: Artificial Sequence
<220> FEATURE:
<223> OTHER INFORMATION: completely synthesized nu cleotide sequence

<400> SEQUENCE: 15
ccgccggcct ggaggagtac ag                                               22

<210> SEQ ID NO 16
<211> LENGTH: 38
<212> TYPE: DNA
<213> ORGANISM: Artificial Sequence
<220> FEATURE:
<223> OTHER INFORMATION: completely synthesized nu cleotide sequence

<400> SEQUENCE: 16
gagagaattc gccaccatga ctgagtacaa actggtgg                              38

<210> SEQ ID NO 17
<211> LENGTH: 32
<212> TYPE: DNA
<213> ORGANISM: Artificial Sequence
<220> FEATURE:
<223> OTHER INFORMATION: completely synthesized nu cleotide sequence

<400> SEQUENCE: 17
gagagtcgac ttgttacatc accacacatg gc                                    32

<210> SEQ ID NO 18
<211> LENGTH: 21
<212> TYPE: DNA
<213> ORGANISM: Artificial Sequence
<220> FEATURE:
<223> OTHER INFORMATION: completely synthesized nu cleotide sequence

<400> SEQUENCE: 18
gttggagcag ttggtgttgg g                                                21

<210> SEQ ID NO 19
<211> LENGTH: 38
<212> TYPE: DNA
<213> ORGANISM: Artificial Sequence
<220> FEATURE:
<223> OTHER INFORMATION: completely synthesized nu cleotide sequence

<400> SEQUENCE: 19
gagaggtacc gccaccatga ctgaatataa acttgtgg                              38
```

```
<210> SEQ ID NO 20
<211> LENGTH: 36
<212> TYPE: DNA
<213> ORGANISM: Artificial Sequence
<220> FEATURE:
<223> OTHER INFORMATION: completely synthesized nu cleotide sequence

<400> SEQUENCE: 20
ctctgtcgac gtatttacat aattacacac tttgtc                                 36

<210> SEQ ID NO 21
<211> LENGTH: 24
<212> TYPE: DNA
<213> ORGANISM: Artificial Sequence
<220> FEATURE:
<223> OTHER INFORMATION: completely synthesized nu cleotide sequence

<400> SEQUENCE: 21
gtagttggag ctgttggcgt aggc                                              24
```

INHIBITORS OF PRENYL-PROTEIN TRANSFERASE

RELATED APPLICATION

This application is filed under 35 U.S.C. 0 371 and is based on International Application Ser. No. PCT/US98/17696, filed on Aug. 26, 1998, and claiming priority to U.S. Provisional application Ser. No. 60/057,080, filed Aug. 27, 1997.

BACKGROUND OF THE INVENTION

The present invention relates to certain compounds that are useful for the inhibition of prenyl-protein transferases and the treatment of cancer. In particular, the invention relates to prenyl-protein transferase inhibitors which are efficacious in vivo as inhibitors of geranylgeranyl-protein transferase type I (GGTase-I) and that inhibit the cellular processing of both the H-Ras protein and the K4B-Ras protein.

Prenylation of proteins by prenyl-protein transferases represents a class of post-translational modification (Glomset, J. A., Gelb, M. H., and Farnsworth, C. C. (1990). Trends Biochem. Sci. 15, 139–142; Maltese, W. A (1990). FASEB J. 4, 3319–3328). This modification typically is required for the membrane localization and function of these proteins. Prenylated proteins share characteristic C-terminal sequences including CAAX (C, Cys; A, an aliphatic amino acid; X, another amino acid), XXCC, or XCXC. Three post-translational processing steps have been described for proteins having a C-terminal CAAX sequence: addition of either a 15 carbon (farnesyl) or 20 carbon (geranylgeranyl) isoprenoid to the Cys residue, proteolytic cleavage of the last 3 amino acids, and methylation of the new C-terminal carboxylate (Cox, A. D. and Der, C. J. (1992a). Critical Rev. Oncogenesis 3:365–400; Newman, C. M. H. and Magee, A. I. (1993). Biochem. Biophys. Acta 1155:79–96). Some proteins may also have a fourth modification: palmitoylation of one or two Cys residues N-terminal to the farnesylated Cys. While some mammalian cell proteins terminating in XCXC are carboxymethylated, it is not clear whether carboxy methylation follows prenylation of proteins terminating with a XXCC motif (Clarke, S. (1992). Annu. Rev. Biochem. 61, 355–386). For all of the prenylated proteins, addition of the isoprenoid is the first step and is required for the subsequent steps (Cox, A. D. and Der, C. J. (1992a). Critical Rev. Oncogenesis 3:365–400; Cox, A. D. and Der, C. J. (1992b) Current Opinion Cell Biol. 4:1008–1016).

Three enzymes have been described that catalyze protein prenylation: farnesyl-protein transferase (FPTase), geranylgeranyl-protein transferase type I (GGPTase-I), and geranylgeranyl-protein transferase type-II (GGPTase-II, also called Rab GGPTase). These enzymes are found in both yeast and mammalian cells (Clarke, 1992; Schafer, W. R. and Rine, J. (1992) Annu. Rev. Genet. 30:209–237). Each of these enzymes selectively uses farnesyl diphosphate or geranylgeranyl diphosphate as the isoprenoid donor and selectively recognizes the protein substrate. FPTase farnesylates CaaX-containing proteins that end with Ser, Met, Cys, Gin or Ala. For FPTase, CaaX tetrapeptides comprise the minimum region required for interaction of the protein substrate with the enzyme. The enzymological characterization of these three enzymes has demonstrated that it is possible to selectively inhibit one with little inhibitory effect on the others (Moores, S. L., Schaber, M. D., Mosser, S. D., Rands, E., O'Hara, M. B., Garsky, V. M., Marshall, M. S., Pompliano, D. L., and Gibbs, J. B., J. Biol. Chem., 266:17438 (1991), U.S. Pat. No. 5,470,832).

The prenylation reactions have been shown genetically to be essential for the function of a variety of proteins (Clarke, 1992; Cox and Der, 1992a; Gibbs, J. B. (1991). Cell 65: 1–4; Newman and Magee, 1993; Schafer and Rine, 1992). This requirement often is demonstrated by mutating the CaaX Cys acceptors so that the proteins can no longer be prenylated. The resulting proteins are devoid of their central biological activity. These studies provide a genetic "proof of principle" indicating that inhibitors of prenylation can alter the physiological responses regulated by prenylated proteins.

The Ras protein is part of a signaling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation, Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willunsen, Ann. Rev. Biochem. 62:851–891 (1993)). Activation of Ras leads to activation of multiple intracellular signal transduction pathways, including the MAP Kinase pathway and the Rho/Rac pathway (Joneson et al., Science 271:810–812).

Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

The Ras protein is one of several proteins that are known to undergo post-translational modification. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci USA, 87:7541–7545 (1990)).

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). Direct inhibition of farnesyl-protein transferase would be more specific and attended by fewer side effects than would occur with the required dose of a general inhibitor of isoprene biosynthesis.

Other farnesylated proteins include the Ras-related GTP-binding proteins such as RhoB, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above.

Inhibitors of farnesyl-protein transferase (FPTase) have been described in two general classes. The first class includes analogs of farnesyl diphosphate (FPP), while the second is related to protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)).

Mammalian cells express four types of Ras proteins (H-, N-, K4A-, and K4B-Ras) among which K4B-Ras is the most frequently mutated form of Ras in human cancers. The genes that encode these proteins are abbreviated H-ras, N-ras, K4A-ras and K4B-ras respectively. H-ras is an abbreviation for Harvey-ras. K4A-ras and K4B-ras are abbreviations for the Kirsten splice variants of ras that contain the 4A and 4B exons, respectively. Inhibition of farnesyl-protein transferase has been shown to block the growth of H-ras-transformed cells in soft agar and to modify other aspects of their transformed phenotype. It has also been demonstrated that certain inhibitors of farnesyl-protein transferase selectively block the processing of the H-Ras oncoprotein intracellularly (N. E. Kohl et al., Science, 260:1934–1937 (1993) and G. L. James et al., Science, 260:1937–1942 (1993). Recently, it has been shown that an inhibitor of farnesyl-protein transferase blocks the growth of H-ras-dependent tumors in nude mice (N. E. Kohl et al., Proc. Natl. Acad. Sci U.S.A, 91:9141–9145 (1994) and induces regression of mammary and salivary carcinomas in H-ras transgenic mice (N. E. Kohl et al., Nature Medicine, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Inhibition of farnesyl pyrophosphate biosynthesis by inhibiting HMG-CoA reductase blocks Ras membrane localization in cultured cells.

It has been disclosed that the lysine-rich region and terminal CVIM sequence of the C-terminus of K-RasB confer resistance to inhibition of the cellular processing of that protein by certain selective FPTase inhibitors. James, et al., J. Biol. Chem. 270, 6221 (1995) Those FPTase inhibitors were effective in inhibiting the processing of H-Ras proteins. James et al., suggested that prenylation of the K4B-Ras protein by GGTase contributed to the resistance to the selective FPTase inhibitors.

Several groups of scientists have recently disclosed compounds that are non-selective FPTase/GGTase inhibitors. (Nagasu et al. Cancer Research, 55:5310–5314 (1995); PCT application WO 95/25086).

It is the object of the instant invention to provide a prenyl-protein transferase inhibitor which is efficacious in vivo as an inhibitor of geranylgeranyl-protein transferase type I (GGTase-I), also known as CAAX GGTase.

It is also the object of the present invention to provide a compound which inhibits the cellular processing of both the H-Ras protein and the K4B-Ras protein.

It is also the object of the present invention to provide a compound which is efficacious in vivo as an inhibitor of the growth of cancer cells characterized by a mutated K4B-Ras protein.

A composition which comprises such an inhibitor compound is used in the present invention to treat cancer.

SUMMARY OF THE INVENTION

The present invention comprises peptidomimetic piperazinone-containing compounds which inhibit the prenyl-protein transferases: farnesyl-protein transferase and geranylgeranyl-protein transferase type I. Further contained in this invention are chemotherapeutic compositions containing these prenyl transferase inhibitors and methods for their production.

The compounds of this invention are illustrated by the formula I:

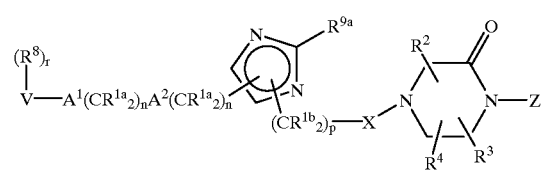

DETAILED DESCRIPTION OF THE INVENTION

The compounds of this invention are useful in the inhibition of prenyl-protein transferases and the prenylation of the oncogene protein Ras. In a first embodiment of this invention, the inhibitors of prenyl-protein transferases are illustrated by the formula I:

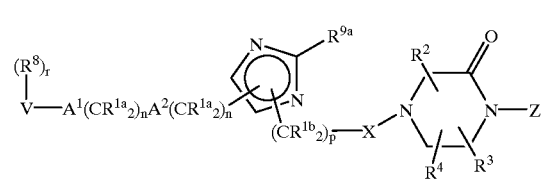

wherein:
  $R^{1a}$ is selected from: hydrogen or $C_1$–$C_6$ alkyl;
  $R^{1b}$ is independently selected from:
    a) hydrogen,
    b) aryl, heterocycle, cycloalkyl, $R^{10}O$—, —$N(R^{10})_2$ or $C_2$–$C_6$ alkenyl,
    c) $C_1$–$C_6$ alkyl unsubstituted or substituted by aryl, heterocycle, cycloalkyl, alkenyl, $R^{10}O$—, or —$N(R^{10})_2$;
  $R^3$ and $R^4$ selected from H and $CH_3$;
  $R^2$ is selected from H; unsubstituted or substituted aryl, unsubstituted or substituted heteroaryl,

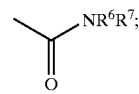

or $C_{1-5}$ alkyl, unbranched or branched, unsubstituted or substituted with one or more of:
  1) aryl,
  2) heterocylce,
  3) $OR^6$,
  4) $SR^{6a}$, $SO_2R^{6a}$, or

5)

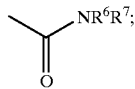

and R² and R³ are optionally attached to the same carbon atom;

R⁶ and R⁷ are independently selected from:
H; $C_{1-4}$ alkyl, $C_{3-6}$ cycloalkyl, aryl, heterocycle, unsubstituted or substituted with:
a) $C_{1-4}$ alkoxy,
b) halogen,
c) perfluoro-$C_{1-4}$ alkyl, or
d) aryl or heterocycle;

$R^{6a}$ is selected from:
$C_{1-4}$ alkyl or $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;

$R^{10}$ is independently selected from hydrogen, $C_1$–$C_6$ alkyl, $C_1$–$C_6$ perfluoroalkyl, 2,2,2-trifluoroethyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —C(O)NR¹⁰—, O, —N(R¹⁰)—, or $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;

X is —CH₂— or —C(=O)—;

Z is selected from:
1) a unsubstituted or substituted group selected from aryl, heteroaryl, arylmethyl, heteroarylmethyl, arylsulfonyl, heteroarylsulfonyl, wherein the substituted group is substituted with one or more of the following:
a) $C_{1-4}$ alkyl, unsubstituted or substituted with:
$C_{1-4}$ alkoxy, NR⁶R⁷, $C_{3-6}$ cycloalkyl, unsubstituted or substituted aryl, heterocycle, HO, —$S(O)_mR^{6a}$, or —C(O)NR⁶R⁷,
b) aryl or heterocycle,
c) halogen,
d) OR⁶,
e) NR⁶R⁷,
f) CN,
g) NO₂,
h) CF₃;
i) —$S(O)_mR^{6a}$,
j) —C(O)NR⁶R⁷, or
k) $C_3$–$C_6$ cycloalkyl; or 2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
a) $C_{1-4}$ alkoxy,
b) NR⁶R⁷,
c) $C_{3-6}$ cycloalkyl,
d) —NR⁶C(O)R⁷,
e) HO,
f) —$S(O)_mR^{6a}$,
g) halogen, or
h) perfluoroalkyl;

m is 0, 1 or 2;

n is 0, 1, 2, 3 or 4;

p is 0, 1, 2, 3 or 4; and r is 0 to 5, provided that r is 0 when V is hydrogen;

provided that the substituent $(R^8)_r$—V—$A^1(CR^{1a}_2)_nA^2(CR^{1a}_2)_n$— is not H;

and provided the compound is not selected from:
1-(3-Chlorophenyl)-4-[1-(4-cyanobenzyl)imidazolylmethyl]-2-piperazinone 2(S)-n-Butyl4-(1-naphthoyl)-1-[1-(2-naphthylmethyl)imidazol-5-ylmethyl]-piperazine 2(S)-n-Butyl-1-[1-(4-cyanobenzyl)imidazol-5-ylmethyl]-4-(1-naphthoyl)piperazine 1-[1-(4-Bromobenzyl)imidazol-5-ylmethyl]-2(S)-n-butyl-4-(1-naphthoyl)piperazine 1-{[1-(4-cyanobenzyl)-1H-imidazol-5-yl]acetyl}-2(S)-n-butyl-4-( 1-naphthoyl)piperazine 1-phenyl-4-[1-(4-yanobenzyl)-1H-imidazol-5-ylethyl]-piperazin-2-one 1-(3-trifluoromethylphenyl)-4-[1-(4-cyanobenzyl)-1H-imidazol-5-ylmethyl]-piperazin-2-one 1-(3-bromophenyl)-4-[1-(4-cyanobenzyl)-1H-imidazol-5-ylmethyl]-piperazin-2-one 5(S)-(2-[2,2,2-trifluoroethoxy]ethyl)-1-(3-triluoromethylphenyl)-4-[1-(4-cyanobenzyl)-4-imidazolylmethyl-piperazin-2-one 1-(5,6,7,8-tetrahydronaphthyl)4-[1-(4-cyanobenzyl)-1H-imidazol-5-ylmethyl]-piperazin-2-one 1-(2-methyl-3-chlorophenyl)4-[1-(4-cyanobenzyl)4-imidazolylmethyl)]-piperazin-2-one or the pharmaceutically acceptable salts thereof.

A preferred embodiment of the compounds of this invention is illustrated by the following formula I-a:

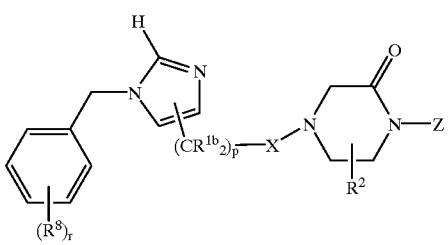

I-a wherein:
R$^{1b}$ is independently selected from:
a) hydrogen,
b) aryl, heterocycle, cycloalkyl, R$^{10}$O—, —N(R$^{10}$)$_2$ or C$_2$–C$_6$ alkenyl,
c) C$_1$–C$_6$ alkyl unsubstituted or substituted by aryl, heterocycle, cycloalkyl, alkenyl, R$^{10}$O—, or —N(R$^{10}$)$_2$;

R$^2$ is selected from H; unsubstituted or substituted aryl or C$_{1-5}$ alkyl, unbranched or branched, unsubstituted or substituted with one or more of:
1) aryl,
2) heteroaryl,
3) OR$^6$, or
4) SR$^{6a}$;

R$^6$ and R$^7$ are independently selected from: C$_{1-4}$ alkyl, aryl, and heteroaryl, unsubstituted or substituted with:
a) C$_{1-4}$ alkoxy,
b) halogen,
c) perfluoro-C$_{1-4}$ alkyl, or
d) aryl or heteroaryl;

R$^{6a}$ is selected from:
C$_{1-4}$ alkyl, unsubstituted or substituted with:
a) C$_{1-4}$alkoxy, or
b) aryl or heteroaryl;

R$^8$ is independently selected from:
a) hydrogen,
b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)2, or R$^{11}$OC(O)NR$^{10}$—, and
c) C$_1$–C$_6$ alkyl substituted by C$_1$–C$_6$ perfluoroalkyl, R$^{10}$O—, R$^{10}$C(O)NR$^{10}$—,(R$^{10}$)$_2$N—C(NR$^{10}$)—, R$^{10}$C(O)—, —N(R$^{10}$)$_2$, or R$^{11}$OC(O)NR$^{10}$—;

R$^{10}$ is independently selected from hydrogen, C$_1$–C$_6$ alkyl, benzyl and aryl;
R$^{11}$ is independently selected from C$_1$–C$_6$ alkyl and aryl;
X is —CH$_2$— or —C(=O)—;
Z is an unsubstituted or substituted group selected from aryl, arylmethyl and arylsulfonyl, wherein the substituted group is substituted with one or more of the following:
a) C$_{1-4}$ alkyl, unsubstituted or substituted with:
C$_{1-4}$ alkoxy, NR$^6$R$^7$, C$_{3-6}$ cycloalkyl, unsubstituted or substituted aryl, heterocycle, HO, —S(O)$_m$R$^{6a}$, or —C(O)NR$^6$R$^7$,
b) aryl or heterocycle,
c) halogen,
d) OR$^6$,
e) NR$^6$R$^7$,
f) CN,
g) NO$_2$,
h) CF$_3$;
i) —S(O)$_m$R$^{6a}$,
j) —C(O)NR$^6$R$^7$, or
k) C$_3$–C$_6$ cycloalkyl;
m is 0, 1 or 2; and
p is 0, 1, 2, 3 or 4; and
r is 0 to 3;

and provided the compound is not selected from:

1-(3-Chlorophenyl)-4-[1-(4-cyanobenzyl) imidazolylmethyl]-2-piperazinone

2(S)-n-Butyl-4-(1-naphthoyl)-1-[1-(2-naphthylmethyl) imidazol-5-ylmethyl]-piperazine 2(S)-n-Butyl-1-[1-(4-cyanobenzyl)imidazol-5-ylmethyl]-4-(1-naphthoyl)piperazine 1-[1-(4-Bromobenzyl)imidazol-5-ylmethyl]-2(S)-n-butyl-4-(1-naphthoyl)piperazine 1-{[1-(4-cyanobenzyl)-1H-imidazol-5-yl]acetyl}-2(S)-n-butyl-4-(l1-naphthoyl)piperazine 1-phenyl-4-[1-(4-cyanobenzyl)-1H-imidazol-5-ylethyl]-piperazin-2-one 1-(3-trifluoromethylphenyl)-4-[1-(4-cyanobenzyl)-1H-imidazol-5-ylmethyl]-piperazin-2-one 1-(3-bromophenyl)-4-[1-(4-cyanobenzyl)-1H-imidazol-5-ylmethyl]- piperazin-2-one 5(S)-(2-[2,2,2-trifluoroethoxylethyl)-1-(3-trifluoromethylphenyl)- 4-[1-(4-cyanobenzyl)-4-imidazolylmethyl]-piperazin-2-one 1-(5,6,7,8-tetrahydronaphthyl)-4-[1-(4-cyanobenzyl)-1H-imidazol-5-ylmethyl]-piperazin-2-one 1-(2-methyl-3-chlorophenyl)-4-[1-(4-cyanobenzyl)-4-imidazolylmethyl)]-piperazin-2-one or the pharmaceutically acceptable salts thereof.

The preferred compounds of this invention are as follows:

1-(3-Trifluoromethoxyphenyl)4-[1-(4-cyanobenzyl) imidazolylmethyl]-2-piperazinone

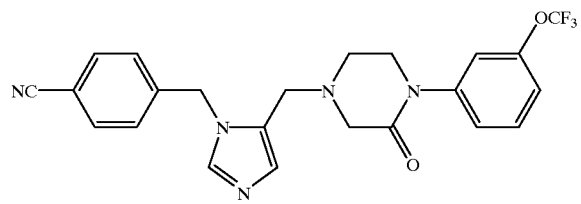

1-(2,5Dimethylphenyl)-4-[1-(4-cyanobenzyl) imidazolylmethyl]-2-piperazinone

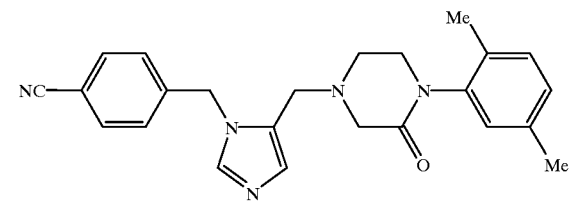

1-(3-Methylphenyl)-4-[1-(4-cyanobenzyl) imidazolylmethyl]-2-piperazinone

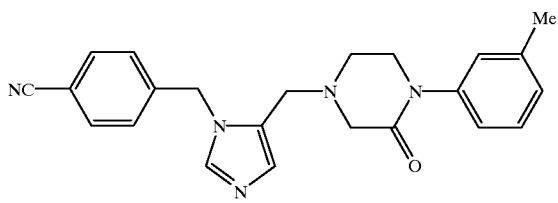

1-(3-Iodophenyl)-4-[1-(4-cyanobenzyl)imidazolylmethyl]-2-piperazinone

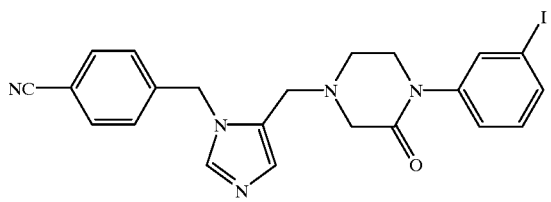

1-(3-Chlorophenyl)-4-[1-(3-methoxy-4-cyanobenzyl)imidazolylmethyl]-2-piperazinone

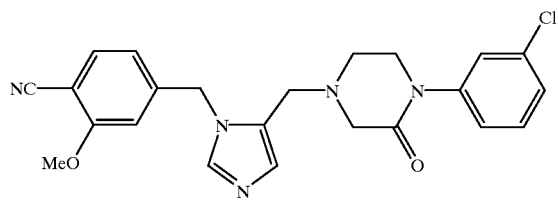

1-(3-Trifluoromethoxyphenyl)-4-[1-(3-methoxy-4-cyanobenzylimidazo)ylmethyl]-2-piperazinone and

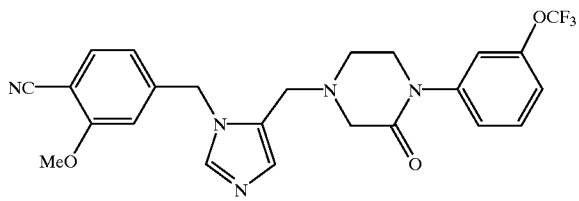

(R)-5-[(Benzyloxy)methyl]-1-(3-chlorophenyl)-4-[1-(4-cyanobenzyl)-imidazolylmethyl]-2- piperazinone

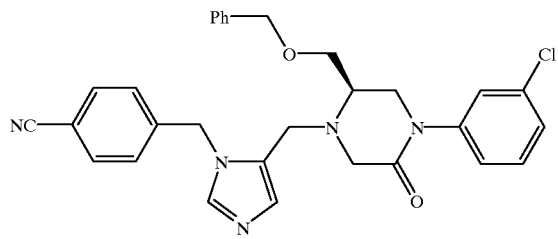

or the pharmaceutically acceptable salts or optical isomers thereof.

Other specific examples of compounds of this invention are:

1-(3-Chlorophenyl)-4-[1-(2-fluoro-4-cyanobenzyl)-1H-imidazol-5-ylmethyl]piperazin-2-one
4-[1-(4-Cyanobenzyl)-1H-imidazol-5-ylmethyl]-1-(3-methylthiophenyl)piperazin-2-one
4-[1-(4-Cyanobenzyl)-1H-imidazol-5-ylmethyl]-1-(3,5-dichlorophenyl)piperazin-2-one
1-(3-Chlorophenyl)-4-{[1-(4-cyanophenyl)-1-ethyl]-1H-imidazol-5-ylmethyl)piperazin-2-one
1-(3-Chloro-4-fluorophenyl)-4-1-(4-cyanobenzyl)-1H-imidazol-5-ylmethyl]-piperazin-2-one
4-[1-(4-Cyanobenzyl)-1H-imidazol-5-ylmethyl]-1-(3,5-dimethylphenyl)piperazin-2-one
(S)-5-Benzyl-4-[3-(4-cyanobenzyl-1-imidazol-5-yl)prop-1-yl) -1-phenyl-2-piperazinone
1-(3-Chlorophenyl)-4-[1-(4-nitrobenzyl)-1H-imidazol-5-ylmethyl]piperazin-2-one
4-[1-(4-Cyanobenzyl)-1H-imidazol-5-ylmethyl]-1-(3,5-difluorophenyl)piperazin-2-one
4-[1-(4-Cyanobenzyl)-1H-imidazol-5-ylmethyl]-1-(3,4-difluorophenyl)piperazin-2-one or the pharmaceutically acceptable salts or optical isomers thereof.

The compounds of the instant invention differ from previously disclosed piperazinone-containing compounds, (PCT Publ. No. WO 97/30343—Oct. 3, 1996; PCT Publ. No. WO 97136593—Oct. 9, 1997; PCT Publ. No. WO 97/36592—Oct. 9, 1997) that were described as selective inhibitors of farnesyl-protein transferase, in that the instant compounds are dual inhibitors of farnesyl-protein transferase and geranylgeranyl-protein transferase type I (GGTase-I). Preferably, the compounds of the instant invention inhibit FPTase in vitro (Example 15) at an $IC_{50}$ of less than 1 mM, inhibit GGTase-I in vitro (Example 16) at an $IC_{50}$ of less than 1 mM and inhibited the cellular processing (farnesylation) of H-Ras (Example 17) at an $IC_{50}$ of less than 1 mM.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^1$, $R^2$ etc.) occurs more than one time in any constituent, its definition on each occurrence is independent at every other occurrence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the definition of $R^2$ and $R^4$, the term "the substituted group" intended to mean a substituted $C_{1-8}$ alkyl, substituted $C_{2-8}$ alkenyl, substituted $C_{2-8}$ alkynyl, substituted aryl or substituted heterocycle from which the substituent(s) $R^2$ and $R^3$ are selected.

As used herein in the definition of $R^6$, $R^{6a}$, $R^7$ and $R^{7a}$, the substituted $C_{1-8}$ alkyl, substituted $C_{3-6}$ cycloalkyl, substituted aryl, substituted aryl, substituted heteroaroyl, substituted arylsulfonyl, substituted heteroarylsulfonyl and substituted heterocycle include moieties containing from 1 to 3 substituents in addition to the point of attachment to the rest of the compound. Preferably, such substituents are selected from the group which includes but is not limited to F, Cl, Br, $CF_3$, $NH_2$, $N(C_1-C_6 \text{ alkyl})_2$, $NO_2$, CN, $(C_1-C_6 \text{ alkyl})O$—, —OH, $(C_1-C_6 \text{ alkyl})S(O)_m$—, $(C_1-C_6 \text{ alkyl})C(O)NH$—, $H_2N$—C(NH)—, $(C_1-C_6 \text{ alkyl})C(O)$—, $(C_1-C_6 \text{ alkyl})OC(O)$—, $N_3$, $(C_1-C_6 \text{ alkyl})OC(O)NH$—, phenyl, pyridyl, imidazolyl, oxazolyl, isoxazolyl, thiazolyl, thienyl, furyl, isothiazolyl and $C_1-C_{20}$ alkyl.

Lines drawn into the ring systems from substituents (such as from $R^2$, $R^3$, $R^4$ etc.) indicate that the indicated bond may be attached to any of the substitutable ring carbon atoms.

Preferably, $R^{1a}$ and $R^{1b}$ are independently selected from: hydrogen, —$N(R^{10})_2$, $R^{10}C(O)NR^{10}$— or unsubstituted or substituted $C_1-C_6$ alkyl wherein the substituent on the substituted $C_1-C_6$ alkyl is selected from unsubstituted or substituted phenyl, —$N(R^{10})_2$, $R^{10}O$— and $R^{10}C(O)NR^{10}$—.

Preferably, $R^2$ is selected from:

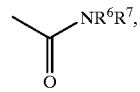

and an unsubstituted or substituted group, the group selected from $C_{1-8}$ alkyl, $C_{2-8}$ alkenyl and $C_{2-8}$ alkynyl;
  wherein the substituted group is substituted with one or more of:
  1) aryl or heterocycle,
  2) $OR^6$,
  3) $SR^{6a}$, $SO_2R^{6a}$,
Preferably, $R^4$ is hydrogen.
Preferably, $R^6$ and $R^7$ are selected from: hydrogen, unsubstituted or substituted $C_1-C_6$ alkyl, unsubstituted or substituted aryl and unsubstituted or substituted $C_3-C_6$ cycloalkyl.
Preferably, $R^6a$ is unsubstituted or substituted $C_1-C_6$.
Preferably, $R^9$ is hydrogen.
Preferably, $R^{10}$ is selected from H, $C_1-C_6$ alkyl and benzyl.
Preferably, $A^1$ and $A^2$ are independently selected from: a bond, —$C(O)NR^{10}$—, —$NR^{10}C(O)$—, O, —$N(R^{10})$—, —$S(O)_2N(R^{10})$— and —$N(R^{10})S(O)_2$—. Most preferably, $A^1$ and $A^2$ are a bond.
Preferably, V is selected from hydrogen, heterocycle and aryl. More preferably, V is phenyl.
Preferably, Z is selected from unsubstituted or substituted phenyl, unsubstituted or substituted naphthyl, unsubstituted or substituted pyridyl, unsubstituted or substituted furanyl and unsubstituted or substituted thienyl. More preferably, Z is unsubstituted or substituted phenyl.
Preferably, n and r are independently 0, 1, or 2.
Preferably p is 1, 2 or 3.
Preferably, the moiety

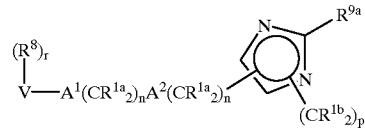

is selected from:

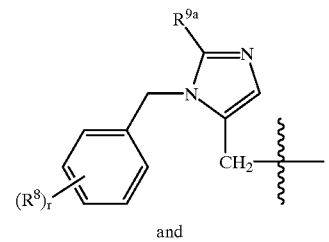

and

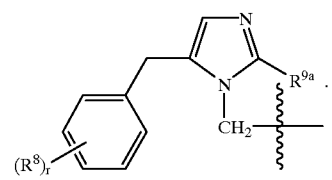

It is intended that the definition of any substituent or variable (e.g., $R^{1a}$, $R^9$, n, etc.) at a particular location in a molecule be independent of its definitions elsewhere in that molecule. Thus, —$N(R^{10})_2$ represents —NHH, —$NHCH_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfamic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–11, in addition to other standard manipulations such as ester hydrolysis, cleavage of protecting groups, etc., as may be known in the literature or exemplified in the experimental procedures. Substituent R, as shown in the Schemes, represents the substituents R$^2$, R$^3$, R$^4$, and R$^5$; however the point of attachment to the ring is illustrative only and is not meant to be limiting.

These reactions may be employed in a linear sequence to provide the compounds of the invention or they may be used to synthesize fragments which are subsequently joined by the reductive alkylation reactions described in the Schemes.

Synopsis of Schemes 1–11:

The requisite intermediates are in some cases commercially available, or can be prepared according to literature procedures, for the most part.

Piperazin-5-ones can be prepared as shown in Scheme 1. Thus, the protected suitably substituted amino acid IV can be converted to the corresponding aldehyde V by first forming the amide and then reducing it with LAH. Reductive amination of Boc-protected amino aldehydes V gives rise to compound VI. The intermediate VI can be converted to a piperazinone by acylation with chloroacetyl chloride to give VII, followed by base-induced cyclization to VIII. Deprotection, followed by reductive alkylation with a protected imidazole carboxaldehyde leads to IX, which can be alkylated with an arylmethylhalide to give the imidazolium salt X. Final removal of protecting groups by either solvolysis with a lower alkyl alcohol, such as methanol, or treatment with triethylsilane in methylene chloride in the presence of trifluoroacetic acid gives the final product XI.

The intermediate VIII can be reductively alkylated with a variety of aldehydes, such as XII. The aldehydes can be prepared by standard procedures, such as that described by O. P. Goel, U. Krolls, M. Stier and S. Kesten in *Organic Syntheses,* 1988, 67, 69–75, from the appropriate amino acid (Scheme 2). The reductive alkylation can be accomplished at pH 5–7 with a variety of reducing agents, such as sodium triacetoxyborohydride or sodium cyanoborohydride in a solvent such as dichloroethane, methanol or dimethylformamide. The product XIII can be deprotected to give the final compounds XIV with trifluoroacetic acid in methylene chloride. The final product XIV is isolated in the salt form, for example, as a trifluoroacetate, hydrochloride or acetate salt, among others. The product diamine XIV can further be selectively protected to obtain XV, which can subsequently be reductively alkylated with a second aldehyde to obtain XVI. Removal of the protecting group, and conversion to cyclized products such as the dihydroimidazole XVII can be accomplished by literature procedures.

Alternatively, the imidazole acetic acid XVIII can be converted to the acetate XIX by standard procedures, and XIX can be first reacted with an alkyl halide, then treated with refluxing methanol to provide the regiospecifically alkylated imidazole acetic acid ester XX (Scheme 3). Hydrolysis and reaction with piperazinone VIII in the presence of condensing reagents such as 1-(3-dimethylaminopropyl)-3-ethylcarbodiimide (EDC) leads to acylated products such as XXI.

If the piperazinone VIII is reductively alkylated with an aldehyde which also has a protected hydroxyl group, such as XXI in Scheme 4, the protecting groups can be subsequently removed to unmask the hydroxyl group (Schemes 4, 5). The alcohol can be oxidized under standard conditions to e.g. an aldehyde, which can then be reacted with a variety of organometallic reagents such as Grignard reagents, to obtain secondary alcohols such as XXIV. In addition, the fully deprotected amino alcohol XXV can be reductively alkylated (under conditions described previously) with a variety of aldehydes to obtain secondary amines, such as XXVI (Scheme 5), or tertiary amines.

The Boc protected amino alcohol XXIII can also be utilized to synthesize 2-aziridinylmethylpiperazinones such as XXVII (Scheme 6). Treating XXIII with 1,1'-sulfonyldiimidazole and sodium hydride in a solvent such as dimethylformamide led to the formation of aziridine XXVII. The aziridine reacted in the presence of a nucleophile, such as a thiol, in the presence of base to yield the ring-opened product XXVIII.

In addition, the piperazinone VIII can be reacted with aldehydes derived from amino acids such as O-alkylated tyrosines, according to standard procedures, to obtain compounds such as XXX (Scheme 7). When R' is an aryl group, XXX can first be hydrogenated to unmask the phenol, and the amine group deprotected with acid to produce XXXI. Alternatively, the amine protecting group in XXX can be removed, and O-alkylated phenolic amines such as XXII produced.

Scheme 8 illustrates the use of an optionally substituted homoserine lactone XXXIII to prepare a Boc-protected piperazinone XXXVII. Intermediate XXXVII may be deprotected and reductively alkylated or acylated as illustrated in the previous Schemes. Alternatively, the hydroxyl moiety of intermediate XXXVII may be mesylated and displaced by a suitable nucleophile, such as the sodium salt of ethane thiol, to provide an intermediate XXXVIII. Intermediate XXXVII may also be oxidized to provide the carboxylic acid on intermediate IXL, which can be utilized form an ester or amide moiety.

N-Aralkyl-piperazin-5-ones can be prepared as shown in Scheme 9. Reductive amination of Boc-protected amino aldehydes V (prepared from III as described previously) gives rise to compound XL. This is then reacted with bromoacetyl bromide under Schotten-Baumann conditions; ring closure is effected with a base such as sodium hydride in a polar aprotic solvent such as dimethylformamide to give XLI. The carbamate protecting group is removed under acidic conditions such as trifluoroacetic acid in methylene chloride, or hydrogen chloride gas in methanol or ethyl acetate, and the resulting piperazine can then be carried on to final products as described in Schemes 1–7.

The isomeric piperazin-3-ones can be prepared as described in Scheme 10. The imine formed from arylcarboxamides XLII and 2-aminoglycinal diethyl acetal (XLIII) can be reduced under a variety of conditions, including sodium triacetoxyborohydride in dichloroethane, to give the amine XLIV. Amino acids I can be coupled to amines XLIV under standard conditions, and the resulting amide XLV when treated with aqueous acid in tetrahydrofuran can cyclize to the unsaturated XLVI. Catalytic hydrogenation under standard conditions gives the requisite intermediate XLVII, which is elaborated to final products as described in Schemes 1–7.

Amino acids of the general formula IL which have a sidechain not found in natural amino acids may be prepared by the reactions illustrated in Scheme 11 starting with the readily prepared imine XLVIII.

SCHEME 1

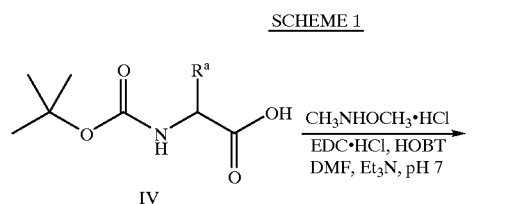

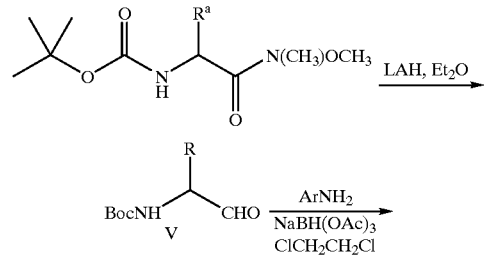

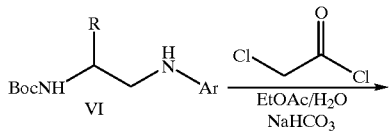

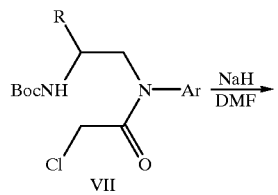

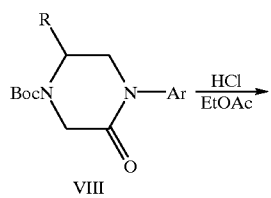

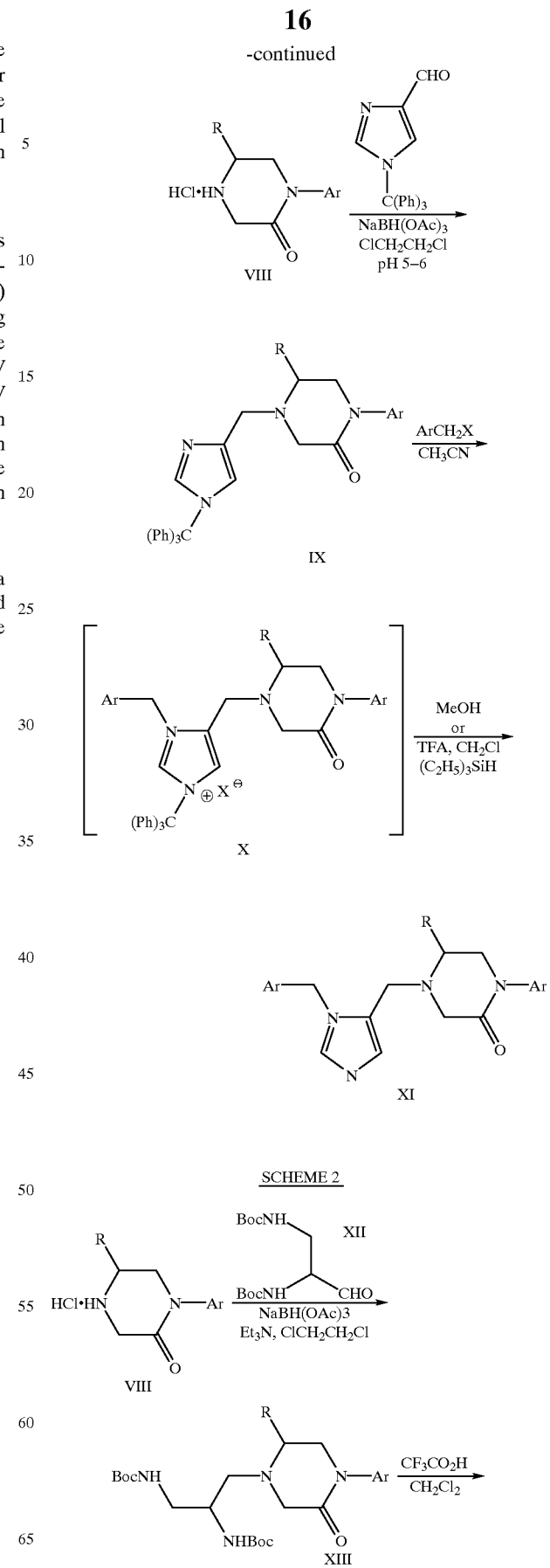

17
-continued
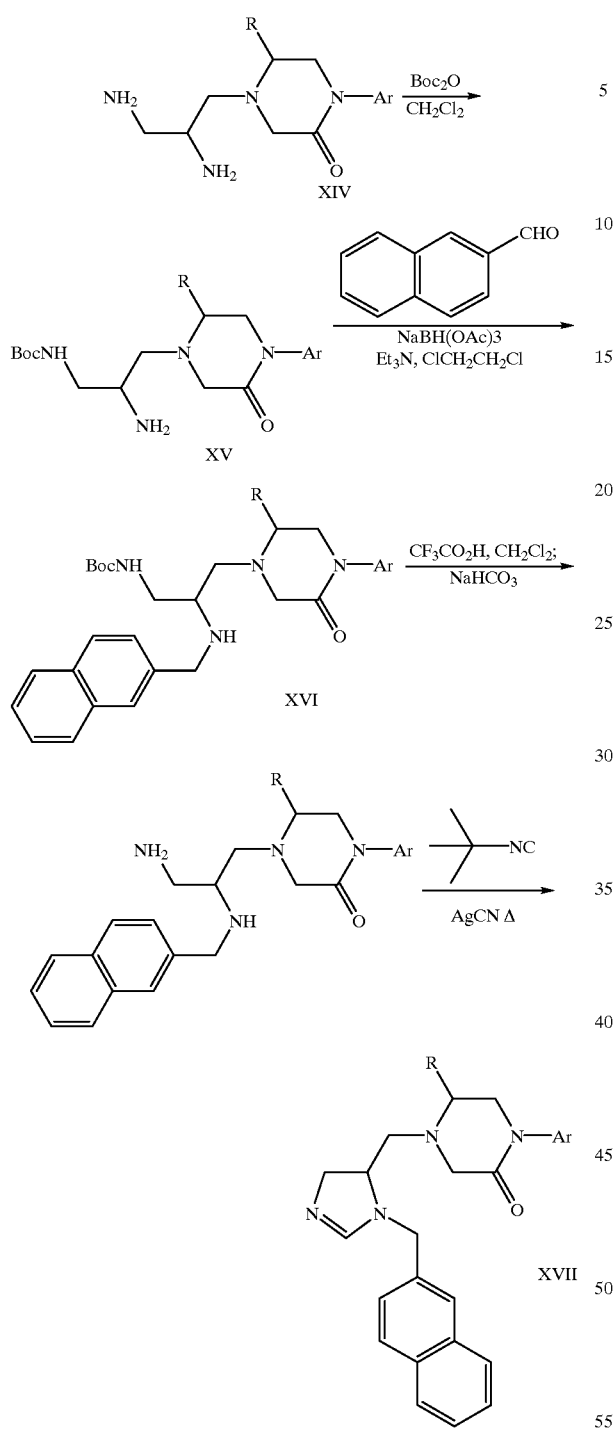
18
-continued
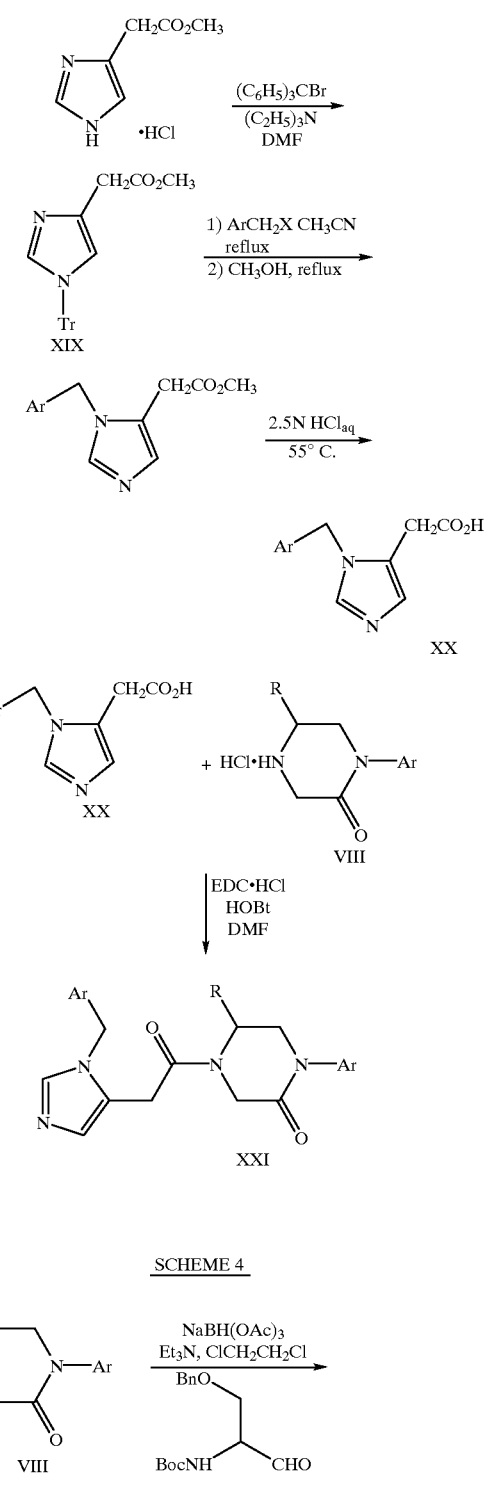
SCHEME 3
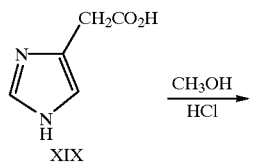
SCHEME 4
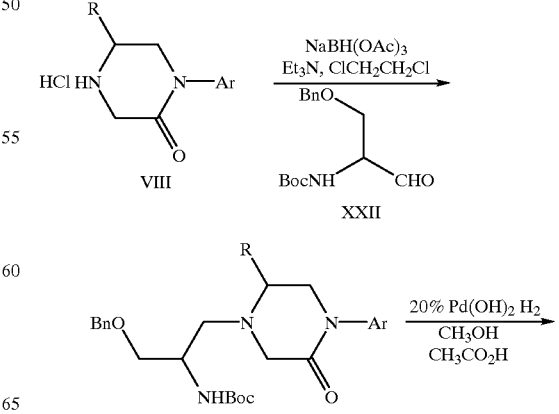

-continued
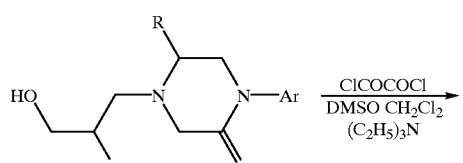
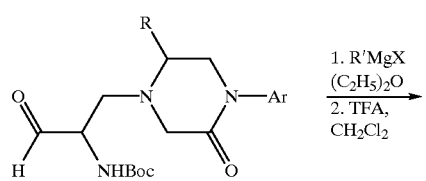
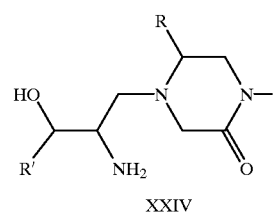
SCHEME 5
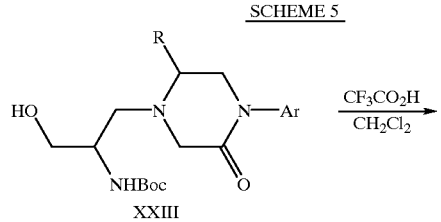
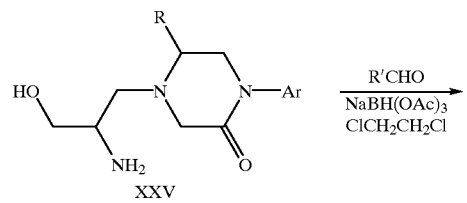
-continued
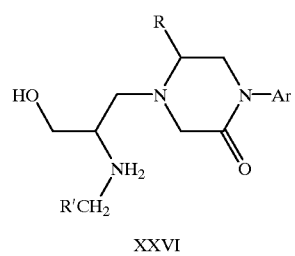
SCHEME 6
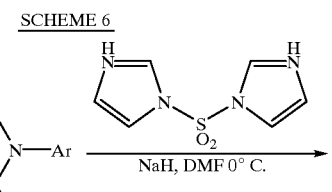
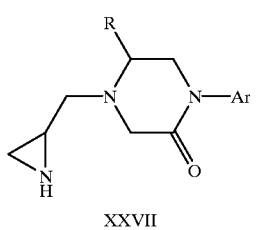
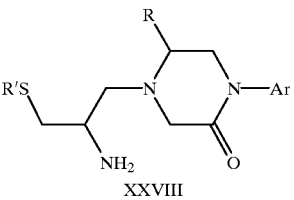
SCHEME 7
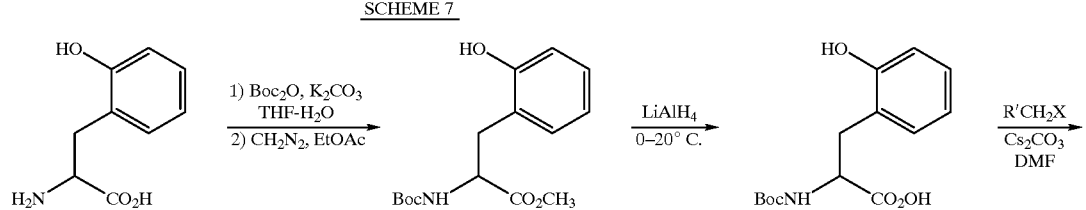

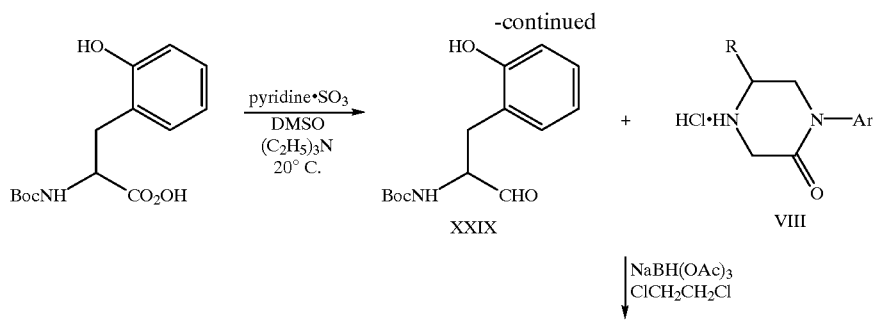
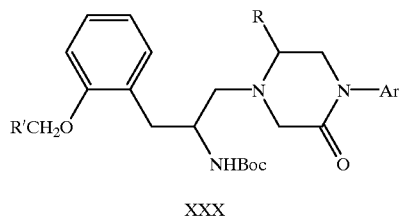
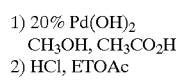
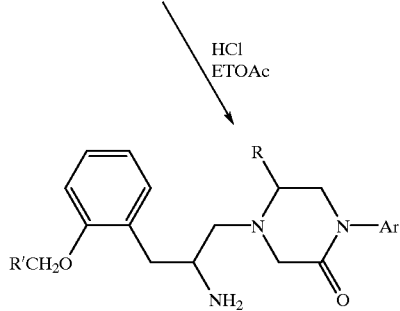
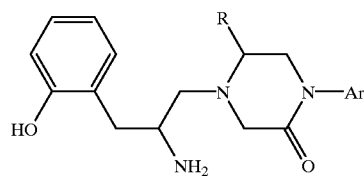
SCHEME 8
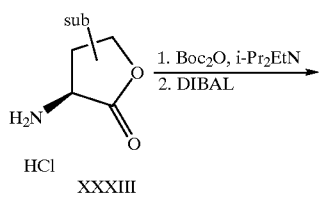
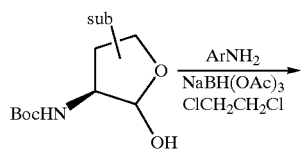
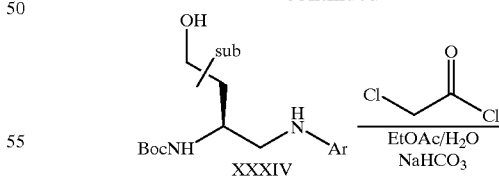
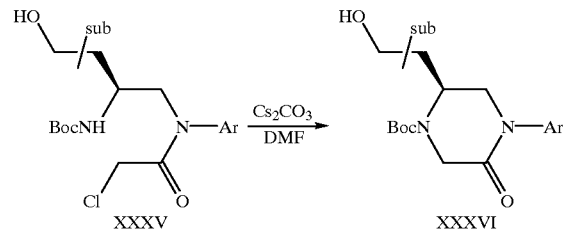

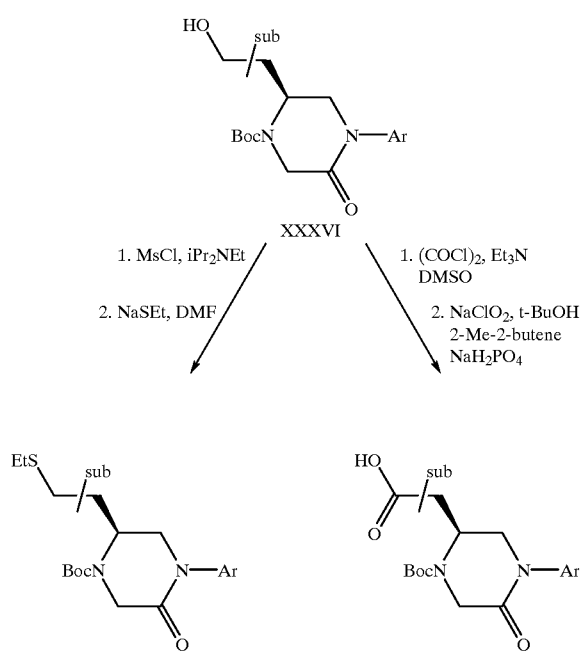

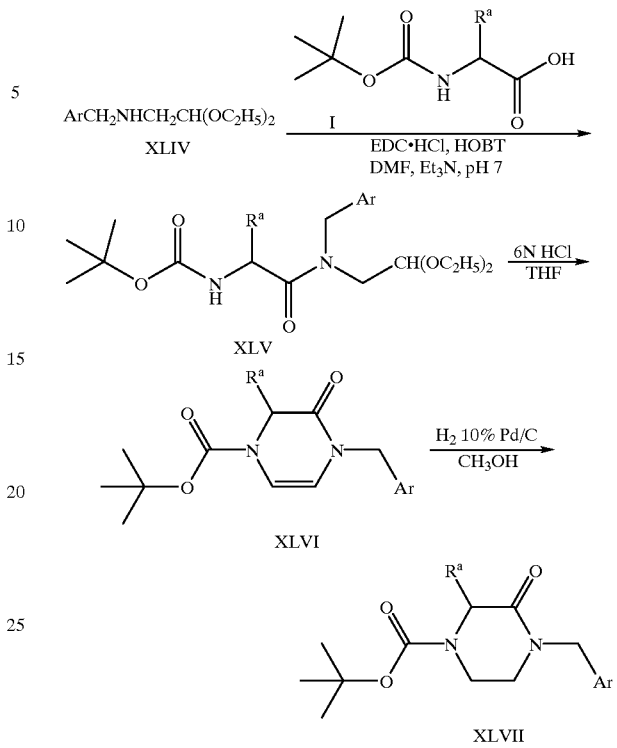

SCHEME 9

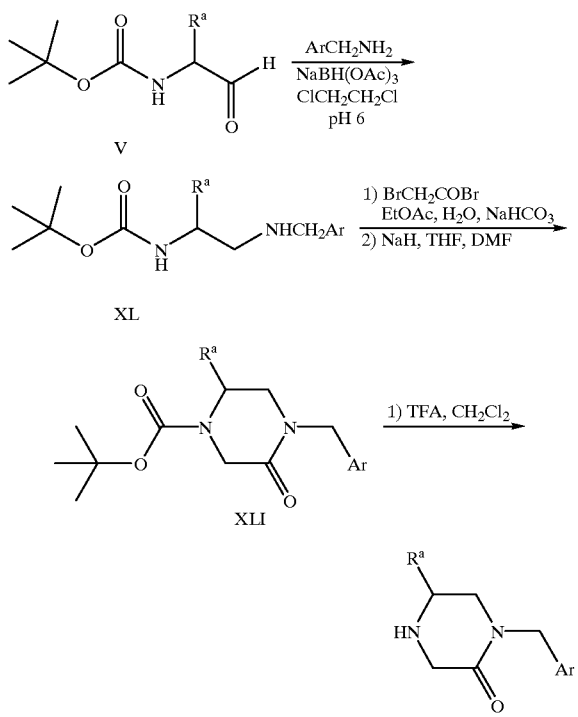

SCHEME 10

SCHEME 11

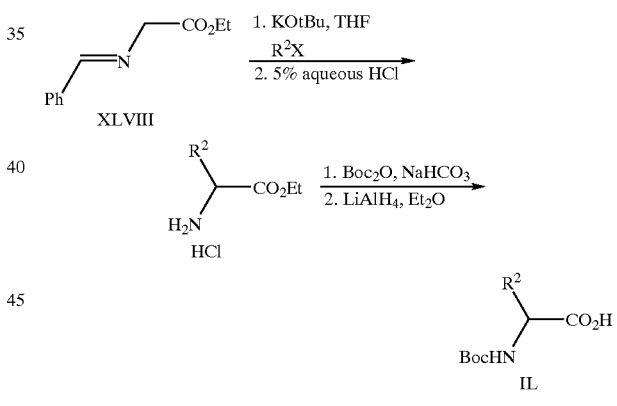

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, src, ab1, Ick, fyn) or by other mechanisms.

The compounds of the instant invention inhibit prenyl-protein transferase and the prenylation of the oncogene protein Ras. The instant compounds may also inhibit tumor angiogenesis, thereby affecting the growth of tumors (J. Rak et al. Cancer Research, 55: 4575–4580 (1995)). Such anti-angiogenesis properties of the instant compounds may also be useful in the treatment of certain forms of vision deficit related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. Science, 256:1331–1333 (1992).

The compounds of the instant invention are also useful in the prevention of restenosis after percutaneous transluminal coronary angioplasty by inhibiting neointimal formation (C. Indolfi et al. Nature medicine, 1:541–545(1995).

The instant compounds may also be useful in the treatment and prevention of polycystic kidney disease (D. L. Schaffner et al. American Journal of Pathology, 142:1051–1060 (1993) and B. Cowley, Jr. et al.FASEB Journal, 2:A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic vascular pathologies.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethylcellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or acetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the instant farnesyl-protein transferase inhibitors and an antineoplastic agent. It is also understood that such a combination of antineoplastic agent and inhibitor of farnesyl-protein transferase may be used in conjunction with other methods of treating cancer and/or tumors, including radiation therapy and surgery.

Examples of an antineoplastic agent include, in general, microtubule-stabilizing agents ( such as paclitaxel (also known as Taxol®), docetaxel (also known as Taxotere®), epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

The preferred class of antineoplastic agents is the taxanes and the preferred antineoplastic agent is paclitaxel.

Radiation therapy, including x-rays or gamma rays which are delivered from either an externally applied beam or by implantation of tiny radioactive sources, may also be used in combination with the instant inhibitor of farnesyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity. The instant compounds may also be co-administered with compounds that are selective inhibitors of geranylgeranyl protein transferase or farnesyl-protein transferase.

In particular, the compounds disclosed in the following patents and publications may be useful as farnesyl pyrophosphate-competitive inhibitor component of the instant composition: U.S. Ser. Nos. 08/254,228 and 08,435,047. Those patents and publications are incorporated herein by reference.

In practicing methods of this invention, which comprise administering, simultaneously or sequentially or in any order, two or more of a protein substrate-competitive inhibitor and a farnesyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and farnesyl pyrophosphate-competitive inhibitor are administered sequentially, the administration of each can be by the same method or by different methods.

The instant compounds may also be useful in combination with an integrin antagonist for the treatment of cancer, as described in U.S. Ser. No. 09/055,487, filed Apr. 6, 1998, which is incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the avb3 integrin, which selectively antagonize, inhibit or counteract binding of a physiological ligand to the avb5 integrin, which antagonize, inhibit or counteract binding of a physiological ligand to both the avb3 integrin and the avb5 integrin, or which antagonize, inhibit or counteract the activity of the particular integrin(s) expressed on capillary endothelial cells. The term also refers to antagonists of the avb6, avb8, a1b1, a2b1, aSb1, a6b1 and a6b4 integrins. The term also refers to antagonists of any combination of avb3, avb5, avb6, avb8, a1b1, a2b1, a5b1, a6b1 and a6b4 integrins. The instant compounds may also be useful with other agents that inhibit angiogenisis and thereby inhibit the growth and invasiveness of tumor cells, including, but not limited to angiostatin and endostatin.

Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the combinations of this invention within the dosage range described below and the other pharmaceutically active agent(s) within its approved dosage range. Combinations of the instant invention may alternatively be used sequentially with known pharmaceutically acceptable agent(s) when a multiple combination formulation is inappropriate.

EXAMPLES

Examples provided are intended to assist in a further understanding of the invention. Particular materials employed, species and conditions are intended to be further illustrative of the invention and not limitative of the reasonable scope thereof.

EXAMPLES 1

1-(3-Chlorophenyl)4-[1-(4-cyanobenzyl)-5-imidazolylmethyl]-2-piperazinone dihydrochloride (Compound 1)

Step A: Preparation of 1-triphenylmethyl-4-(hydroxymethyl)-imidazole

To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: Preparation of 1-triphenylmethyl-4-(acetoxymethyl)-imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a white powder which was sufficiently pure for use in the next reaction.

Step C: Preparation of 1-(4-cyanobenzyl)-5-(acetoxymethyl)-imidazole hydrobromide A solution of the product from Step B (85.8 g, 225 mmol) and a-bromo-p-tolunitrile (50.1 g, 232 mmol) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step D: Preparation of 1-(4-cyanobenzyl)-5-(hydroxymethyl)-imidazole

To a solution of the acetate from Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc ( 3 L), and washed with water, sat. aq. NaHCO$_3$ and brine. The solution was then dried (Na$_2$SO$_4$), filtered, and concentrated in vacuo to provide the crude product as a pale yellow fluffy solid which was sufficiently pure for use in the next step without further purification.

Step E: Preparation of 1-(4-cyanobenzyl)-5-imidazolecarboxaldehyde

To a solution of the alcohol from Step D (21.5 g, 101 mmol) in 500 mL of DMSO at room temperature was added triethylamine (56 mL, 402 mmol), then $SO_3$-pyridine complex (40.5 g, 254 mmol). After 45 minutes,, the reaction was poured into 2.5 L of EtOAc, washed with water (4×1 L) and brine, dried ($Na_2SO_4$), filtered and concentrated in vacuo to provide the aldehyde as a white powder which was sufficiently pure for use in the next step without further purification.

Step F: Preparation of N-(3-chlorophenyl)ethylenediamine hydrochloride

To a solution of 3-chloroaniline (30.0 mL, 284 mmol) in 500 mL of dichloromethane at 0° C. was added dropwise a solution of 4N HCl in 1,4doxane (80 mL, 320 mmol HCl). The solution was warmed to room temperature, then concentrated to dryness in vacuo to provide a white powder. A mixture of this powder with 2-oxazolidinone (24.6 g, 282 mmol) was heated under nitrogen atmosphere at 160° C. for 10 hours, during which the solids melted, and gas evolution was observed. The reaction was allowed to cool, forming the crude diamine hydrochloride salt as a pale brown solid.

Step G: Preparation of N-(tert-butoxycarbonyl)—N'-(3-chlorophenyl)ethylenediamine The amine hydrochloride from Step F (ca. 282 mmol, crude material prepared above) was taken up in 500 mL of THF and 500 mL of sat. aq. $NaHCO_3$ soln., cooled to 0° C., and di-tert-butylpyrocarbonate (61.6 g, 282 mmol) was added. After 30 h, the reaction was poured into EtOAc, washed with water and brine, dried ($Na_2SO_4$), filtered, and concentrated in vacuo to provide the titled carbamate as a brown oil which was used in the next step without further purification.

Step H: Preparation of N-[2-(tert-butoxycarbamoyl)ethyl]-N-(3-chlorophenyl)-2-chloroacetamide A solution of the product from Step G (77 g, ca. 282 mmol) and triethylamine (67 mL, 480 mmol) in 500 mL of $CH_2Cl_2$ was cooled to 0° C. Chloroacetyl chloride (25.5 mL, 320 mmol) was added dropwise, and the reaction was maintained at 0° C. with stirring. After 3 h, another portion of chloroacetyl chloride (3.0 mL) was added dropwise. After 30 min, the reaction was poured into EtOAc (2 L) and washed with water, sat. aq. $NH_4Cl$ soln, sat. aq. $NaHCO_3$ soln., and brine. The solution was dried ($Na_2SO_4$), filtered, and concentrated in vacuo to provide the chloroacetamide as a brown oil which was used in the next step without further purification.

Step I: Preparation of 4-(tert-butoxycarbonyl)-1-(3-chlorophenyl)-2-piperazinone To a solution of the chloroacetamide from Step H (ca. 282 mmol) in 700 mL of dry DMF was added $K_2CO_3$ (88 g, 0.64 mol). The solution was heated in an oil bath at 70–75° C. for 20 hrs., cooled to room temperature, and concentrated in vacuo to remove ca. 500 mL of DMF. The remaining material was poured into 33% EtOAc hexane, washed with water and brine, dried ($Na_2SO_4$), filtered, and concentrated in vacuo to provide the product as a brown oil. This material was purified by silica gel chromatography (25–50% EtOAc/hexane) to yield pure product, along with a sample of product (ca. 65% pure by HPLC) containing a less polar impurity.

Step J: Preparation of 1-(3-chlorophenyl)-2-piperazinone

Through a solution of Boc-protected piperazinone from Step I (17.19 g, 55.4 mmol) in 500 mL of EtOAc at −78° C. was bubbled anhydrous HCl gas. The saturated solution was warmed to 0° C., and stirred for 12 hours. Nitrogen gas was bubbled through the reaction to remove excess HCl, and the mixture was warmed to room temperature. The solution was concentrated in vacuo to provide the hydrochloride as a white powder. This material was taken up in 300 mL of $CH_2Cl_2$ and treated with dilute aqueous $NaHCO_3$ solution. The aqueous phase was extracted with $CH_2Cl_2$ (8×300 mL) until the analysis indicated complete extraction. The combined organic mixture was dried ($Na_2SO_4$), filtered, and concentrated in vacuo to provide the titled free amine as a pale brown oil.

Step K: Preparation of 1-(3-chlorophenyl)-4-[1-(4-cyanobenzyl)-5-imidazolylmethyl]-2-piperazinone dihydrochloride To a solution of the amine from Step J (55.4 mmol, prepared above) in 200 mL of 1,2-dichloroethane at 0° C. was added 4 Å powdered molecular sieves (10 g), followed by sodium triacetoxy-borohydride (17.7 g, 83.3 mmol). The imidazole carboxaldehyde from Step E of Example 1 (11.9 g, 56.4 mmol) was added, and the reaction was stirred at 0° C. After 26 hours, the reaction was poured into EtOAc, washed with dilute aq. $NaHCO_3$, and the aqueous layer was back-extracted with EtOAc. The combined organics were washed with brine, dried ($Na_2SO_4$), filtered, and concentrated in vacuo. The resulting product was taken up in 500 mL of 5:1 benzene:$CH_2Cl_2$, and propylamine (20 mL) was added. The mixture was stirred for 12 hours, then concentrated in vacuo to afford a pale yellow foam. This material was purified by silica gel chromatography (2–7% MeOH/$CH_2Cl_2$), and the resultant white foam was taken up in $CH_2Cl_2$ and treated with 2.1 equivalents of 1M HCl/ether solution. After concentrated in vacuo, the product dihydrochloride was isolated as a white powder.

Examples 2 and 3 (Table 1) were prepared using the above protocol, which describes the synthesis of the structurally related compound Table 1 lists other compounds of the instant invention that were prepared using the procedure described in Example 1. In Step F, the appropriately substituted aniine was used in place of 3-chloroaniline.

TABLE 1

1-Aryl-4-[1-(4-cyanobenzyl)imidazolylmethyl]-2-piperazinones

| Example | X | FAB mass spectrum (M + 1) | CHN Analysis |
|---|---|---|---|
| 2 | 3-$OCF_3$ | 456 | $C_{23}H_{20}F_3N_5O_2$.2.0HCl.0.60$H_2O$ calcd; C, 51.24; H, 4.34; N, 12.99. found; C, 51.31; H, 4.33; N, 12.94. |
| 3 | 2,5-$(CH_3)_2$ | 400 | $C_{24}H_{25}N_5O$.2.00HCl.0.65$H_2O$ calcd; C, 59.54; H, 5.89; N, 14.47 found; C, 59.54; H, 5.95; N, 14.12. |
| 4 | 3-$CH_3$ | 386 | $C_{23}H_{23}N_5O$.2.0HCl.0.80$H_2O$ calcd; C, 58.43; H, 5.67; N, 14.81. found; C, 58.67; H, 6.00; N, 14.23. |
| 5 | 3-I | 498 | $C_{22}H_{20}N_5OI$.2.25HCl.0.90$H_2O$ calcd; C, 44.36; H, 4.07; N, 11.76. found; C, 44.37; H, 4.06; N, 11.42. |

EXAMPLE 6

1-(3-chlorophenyl)-4-[1-(4-cyano-3-methoxybenzyl)-5-imidazolylmethyl]-2-piperazinone dihydrochloride Step A: Preparation of Methyl 4-Amino-3-hydroxybenzoate Through a solution of 4-amino-3-hydroxybenzoic acid (75 g, 0.49 mol) in 2.0 L of dry methanol at room temperature was bubbled anhydrous HCl gas until the solution was saturated. The solution was stirred for 48 hours, then concentrated in vacuo. The product was partitioned between EtOAc and saturated aq. $NaHCO_3$ solution, and the organic layer was washed with brine, dried ($Na_2SO_4$), and concentrated in vacuo to provide the titled compound.

Step B: Preparation of Methyl 3-Hydroxy-4-iodobenzoate

A cloudy, dark solution of the product from Step A (79 g, 0.47 mol), 3N HCl (750 mL), and THF (250 mL) was cooled to 0° C. A solution of $NaNO_2$ (35.9 g, 0.52 mol) in 115 mL of water was added over ca. 5 minutes, and the solution was stirred for another 25 minutes. A solution of potassium iodide (312 g, 1.88 mol) in 235 mL of water was added all at once, and the reaction was stirred for an additional 15 minutes. The mixture was poured into EtOAc, shaken, and the layers were separated. The organic phase was washed with water and brine, dried ($Na_2SO_4$), and concentrated in vacuo to provide the crude product (148 g). Purification by column chromatography through silica gel (0%–50% EtOAc/hexane) provided the titled product.

Step C: Preparation of Methyl 4-Cyano-3-hydroxybenzoate

A mixture of the iodide product from Step B (101 g, 0.36 mol) and zinc(II)cyanide (30 g, 0.25 mol) in 400 mL of dry DMF was degassed by bubbling argon through the solution for 20 minutes. Tetrakis(triphenylphosphine)palladium (8.5 g, 7.2 mmol) was added, and the solution was heated to 80° C. for 4 hours. The solution was cooled to room temperature, then stirred for an additional 36 hours. The reaction was poured into EtOAc water, and the organic layer was washed with brine (4×), dried ($Na_2SO_4$), and concentrated in vacuo to provide the crude product. Purification by column chromatography through silica gel (30%–50% EtOAc/hexane) provided the titled product.

Step D: Preparation of Methyl 4-Cyano-3-methoxybenzoate

Sodium hydride (9 g, 0.24 mol as 60% wt. disp. mineral oil) was added to a solution of the phenol from Step C (36.1 g, 204 mmol) in 400 mL of dry DMF at room temperature. Iodomethane was added (14 mL. 0.22 mol) was added, and the reaction was stirred for 2 hours. The mixture was poured into EtOAc/water, and the organic layer was washed with water and brine (4×), dried ($Na_2SO_4$), and concentrated in vacuo to provide the titled.

Step E: Preparation of 4-Cyano-3-methoxybenzyl Alcohol

To a solution of the ester from Step D (48.8 g, 255 mmol) in 400 mL of dry THF under argon at room temperature was added lithium borohydride (255 mL, 510 mmol, 2M THF) over 5 minutes. After 1.5 hours, the reaction was warmed to reflux for 0.5 hours, then cooled to room temperature. The solution was poured into EtOAc/1N HCl soln. [CAUTION], and the layers were separated. The organic layer was washed with water, sat $Na_2CO_3$ soln. and brine (4×), dried ($Na_2SO_4$), and concentrated in vacuo to provide the titled product.

Step F: Preparation of 4-Cyano-3-methoxybenzyl Bromide

A solution of the alcohol from Step E (35.5 g, 218 mmol) in 500 mL of dry THF was cooled to 0° C. Triphenylphosphine was added (85.7 g, 327 mmol), followed by carbontetrabromide (108.5 g, 327 mmol). The reaction was stirred at 0° C. for 30 minutes, then at room temperature for 21 hours. Silica gel was added (ca. 300 g), and the suspension was concentrated in vacuo. The resulting solid was loaded onto a silica gel chromatography column. Purification by flash chromatography (30%–50% EtOAc/hexane) provided the titled.

Step G: Preparation of 1-(4-cyano-8-methoxybenzyl)-5-(acetoxthyl)-imidazole hydrobromide The titled product was prepared by reacting the bromide from Step F (21.7 g, 96 mmol) with the imidazole product from Step B of Example 1 (34.9 g, 91 mmol) using the procedure outlined in Step C of Example 1. The crude product was triturated with hexane to provide the titled product hydrobromide.

Step H: Preparation of 1-(4-cyano-3-methoxybenzyl)-5-(hydroxyethyl)-imidazole

The titled product was prepared by hydrolysis of the acetate from Step G (19.43 g, 68.1 mmol) using the procedure outlined in Step D of Example 1. The crude titled product was isolated in modest yield (11 g, 66% yield). Concentration of the aqueous extracts provided solid material (ca. 100 g) which contained a significant quantity of the titled product, as judged by $^1H$ NMR spectroscopy.

Step I: Preparation of 1-(4-cyano-3-methoxybenzyl)-5-imidazolecarboxaldehyde

The titled product was prepared by oxidizing the alcohol from Step H (11 g, 45 mmol) using the procedure outlined in Step E of Example 1. The titled aldehyde was isolated as a white powder which was sufficiently pure for use in the next step without further purification.

Step J: Preparation of 1-(3-chlorophenyl)-4-[1-(4-cyano-3-methoxybenzyl)-5-imidazolylmethyl-2-piperazinone dihydrochloride The titled product was prepared by reductive alkylation of the aldehyde from Step I (859 mg, 3.56 mmol) and the amine (hydrochloride) from Step K of Example 1 (800 mg, 3.24 mmol) using the procedure outlined in Step H of Example 1. Purification by flash column chromatography through silica gel (50%–75% acetone $CH_2Cl_2$) and conversion of the resulting white foam to its dihydrochloride salt provided the titled product as a white powder. FAB ms (m+1) 437.

Anal. Calc. for $C_{23}H_{23}ClN_5O_2 \cdot 2.0HCl \cdot 0.35CH_2Cl_2$: C, 51.97; H, 4.80; N, 12.98.

Found: C, 52.11; H, 4.80; N, 12.21.

EXAMPLE 7

1-(3-trifluoromethoxyphenyl)-4-[1-(4-cyano-3-methoxybenzyl)-5-imidazolyl methyl]-2-piperazinone dihydrochloride 1-(3-trifluoromethoxy-phenyl)-2-piperazinone hydrochloride was prepared from 3-trifluoromethoxyaniline using Steps F–J of Example 1. This amine (1.75 g, 5.93 mmol) was coupled to the aldehyde from Step I of Example 6 (1.57 g, 6.52 mmol) using the procedure outlined in Step H of Example 1. Purification by flash column chromatography through silica gel (60%–100% acetone $CH_2Cl_2$) and conversion of the resulting white foam to its dihydrochloride salt provided the titled product as a white powder.

FAB ms (m+1) 486.

Anal. Calc. for $C_{24}H_{23}F_3N_5O_3 \cdot 2.0HCl \cdot 0.60H_2O$: C, 50.64; H, 4.46; N. 12.30.

Found: C, 50.69; H, 4.52; N, 12.13.

EXAMPLE 8

(R)-5-[(Benzyloxy)methyl]-1-(3-chlorophenyl)-4-[1-(4-cyanobenzyl)-5-imidazolylmethyl]-2-piperazinone dihydrochloride Steps A–E: Preparation of (R)-5-[(benzyloxy)methyl]-1-(3-chlorophenyl)-2-piperazinone hydrochloride The titled compound was prepared using an adaptation of the following protocol, which describes the synthesis of the structurally related compound 5(S)-n-butyl-1-(2,3-dimethylphenyl)-2-piperazinone hydrochloride. In Step A, N-Boc-Ser(OBn)—OH was used instead of 2(S)-(butoxycarbonylamino)hexanoic acid.

Step A: N-Methoxy-N-methyl 2(S)-(tert-butoxycarbonylamino)-hexanamide

2(S-(Butoxycarbonylamino)hexanoic acid (24.6 g, 0.106 mol), N,O-dimethylhydroxylamine hydrochloride (15.5 g, 0.15 mol), EDC hydrochloride ( 22.3 g, 0.117 mol) and HOBT (14.3 g, 0.106 mol) were stirred in dry, degassed DMF (300 mL) at 20° C. under nitrogen. N-Methylmorpholine was added to obtain pH 7. The reaction was stirred overnight, the DMF distilled under high vacuum, and the residue partitioned between ethyl acetate and 2% potassium hydrogen sulfate. The organic phase was washed with saturated sodium bicarbonate, water, and saturated brine, and dried with magnesium sulfate. The solvent was removed in vacuo to give the title compound.

Step B: 2(S)-(tert-Butoxycarbonylamino)hexanal

A mechanically stirred suspension of lithium aluminum hydride (5.00 g, 0.131 mol) in ether (250 mL) was cooled to −45"C under nitrogen. A solution of the product from Step A (28.3 g, 0.103 mol) in ether (125 mL) was added, maintaining the temperature below −35° C. when the addition was complete, the reaction was warmed to 5° C., then recooled to −45° C. A solution of potassium hydrogen sulfate (27.3 g, 0.200 mol) in water was slowly added, maintaining the temperature below −5° C. After quenching, the reaction was stirred at room temperature for 1 h. The mixture was filtered through Celite, the ether evaporated, and the remainder partitioned between ethyl acetate and 2% potassium hydrogen sulfate. After washing with saturated brine, drying over magnesium sulfate and solvent removal, the title compound was obtained.

Step C: N-(2,3-Dimethylphenyl)-2(S)-(tert-butoxycarbonylamino)-hexanamine 2,3-Dimethylamine (8.32 mL, 68.3 mmol) was dissolved in dichloroethane under nitrogen. Acetic acid was added to obtain pH 5, and sodium triacetoxyborohydride (17.2 g, 80.8 mmol) and crushed molecular sieves (4 g) were added. A solution of the product from Step B (13.3 g, 62.1 mmol) in dichloroethane (80 mL) was added slowly dropwise at 20° C. The reaction was stirred overnight, then quenched with saturated sodium bicarbonate solution. The aqueous layer was removed, the organic phase washed with saturated brine and dried over magnesium sulfate. Crystallization from hexane gave the title compound.

Step D: 4tert-Butoxycarbonyl-5(S)n-butyl-1-(2,3-dimethylphenyl)-2-piperazinone

A solution of the product from Step C (8.50 g, 26.5 mmol) in ethyl acetate (250 mL) was vigorously stirred at 0° C. with saturated sodium bicarbonate (150 mL). Chloroacetyl chloride (2.33 mL, 29.1 mmol) was added, and the reaction stirred at ) 0° C. for 1 h. The layers were separated, and the ethyl acetate phase was washed with saturated brine, and dried over magnesium sulfate. The crude product was dissolved in DMF (300 mL) and cooled to 0° C. under nitrogen. Sodium hydride (1.79 g, 60% dispersion in oil, 44.9 mmol) was added portionwise to maintain moderate hydrogen evolution. After 30 min, an additional amount of sodium hydride was added (0.8 g). The reaction was stirred another 30 min, then quenched with saturated ammonium chloride. The DMF was distilled in vacuo, and the residue partitioned between ethyl acetate and water. The organic phase was washed with water, saturated brine, and dried over magnesium sulfate. The crude product was chromatographed on silica gel with 20–30% ethyl acetate in hexane to obtain the title compound.

Step E: 5(S)-n-Butyl-1-(2,3-dimethylphenyl)-2-piperazinone

A solution of the product from Step D (0.570 g, 1.58 mmol) in ethyl acetate (50 mL) was cooled to −15° C. under nitrogen. HCl gas was bubbled through for 15 min, and the reaction solution warmed to 0° C. for 2h. The solvent was removed in vacuo to provide the titled product.

Step F: Preparation of (R)-5-[(Benzyloxy)methyl]-1-(3-chlorophenyl)-4-[1-(4-cyanobenzyl)-5-imidazolylmethyl]-2-piperazinone dihydrochloride The titled product was prepared by reductive alkylation of the aldehyde from Step E of Example 1 (181 mg, 0.858 mmol) and (R)-5-[(benzyloxy)methyl]-1-(3-chlorophenyl)-2-piperazinone hydrochloride from the present Example (205 mg, 0.558 mmol) using the procedure outlined in Step K of Example 1. Purification by flash column chromatography through silica gel (acetone/$CH_2Cl_2$) and conversion to the dihydrochloride salt provided the titled product as a white powder. FAB ms (m+1) 526.

Anal. Calc. for $C_{30}H_{28}ClN_5O_2 \cdot 2.15HCl \cdot 0.55H_2O$: C, 58.65; H, 5.13; N, 11.40.

Found: C, 58.63; H, 5.13; N, 11.18.

EXAMPLE 9

1-(3-Chlorophenyl)-4-[1-(4-cyano-3-(trifluoromethoxy)benzyl)-5-imidazolylmethyl-2-piperazinone dihydrochloride Step A: Preparation of 4-bromo-2-(trifluoromethoxy) benzonitrile To a solution of 4-bromo-2-(trifluoromethoxy) iodobenzene (25 g, 68 mmol) and zinc(II) cyanide (4.0 g, 34 mmol) in 150 mL of degassed dimethylformamide was added tetrakis(triphenylphosphine)palladium (3.1 g, 4 mole %). The solution was stirred at 80 ° C. for one hour, then cooled to room temperature. Additional portions of zinc(II) cyanide (800 mg) and tetrakis(triphenylphosphine) palladium (700 mg) were added, and the solution was heated at 80° C. for 3 hours. The mixture was diluted with EtOAc and extracted with saturated $NaHCO_3$ solution and brine, dried over sodium sulfate, filtered, and concentrated in vacuo. Purification by silica gel column chromatography (0–5% ether/hexane) gave the titled product.

Step B: Preparation of methyl 4-cyano-3-(trifluoromethoxy) benzoate

Through a solution of the product from Step A (3.82 g, 14.4 mmol), palladium(II) acetate (150 mg, 0.4 wt %), 1,3-bis(diphenylphosphino)propane (300 mg), and triethylamine (3.5 mL) in 30 mL of MeOH and 15 mL of DMSO was bubbled carbon monoxide gas for 6 hours. The reaction was heated to 80° C. and stirred under a balloon of carbon monoxide. After ca. 16 hours, another additional portions of palladium(II) acetate (100 mg) and 1,3-bis (diphenylphosphino)propane (200 mg) were added, and the solution was stirred for an additional 20 hours. The mixture was diluted with EtOAc and extracted with water and brine, dried over sodium sulfate, filtered, and concentrated in vacuo. Purification by silica gel column chromatography (20% EtOAc/hexane) gave the titled product.

Step C: Preparation of 4-cyano-3-(trifluoromethoxy) benzyl alcohol

To a solution of the product from Step B (4.29 g, 17.5 mmol) in 100 mL of methanol at 0° C. was added sodium borohydride (1.3 g, 35 mmol). The solution was allowed to warm to room temperature over 2 hours. An additional portion of sodium borohydride was added (500 mg), and the solution stirred for 30 minutes. The mixture was diluted with EtOAc and extracted with saturated NaHCO₃ solution and brine, dried over sodium sulfate, filtered, and concentrated in vacuo to give the titled product.

Step D: Preparation of 1-[4-cyano-3-(trifluoromethoxy) benzyl]-5-(acetoxymethyl)-imidazole To a solution of the product from Step C (1.5 g, 6.9 mmol) and the product from Step B of Example 1 (2.6 g, 6.9 mmol) in 10 mL of dichloromethane at −78 °C. was added diisopropylethylamine (2.4 mL, 14 mmol), followed by slow addition of trifluoromethanesulfonic anhydride (1.26 mL, 7.5 mmol). The solution was stirred for 15 minutes, then allowed to warm to room temperature. After 2 hours, methanol was added (10 mL), and the solution was stirred for 48 hours. The reaction was concentrated in vacuo, diluted with EtOAc and extracted with saturated NaHCO₃ solution and brine, dried over sodium sulfate, filtered, and concentrated in vacuo. Purification by silica gel column chromatography (5–10% MeOH/EtOAc) gave the titled product.

Step E: Preparation of 1-[4-cyano3-(trifluoromethoxybenzyl]-5-(hydroxymethyl)-imidazole The titled compound was prepared from the product of Step D (1.94 g, 5.72 mmol) using the procedure described in Step D of Example 1. This provided the titled product.

Step F: Preparation of 1-[4-cyano-3-(trifluoromethoxy) benzyl]imidazole-5-carboxaldehyde The titled compound was prepared from the product of Step E (1.31 g, 4.41 mmol) using the procedure described in Step E of Example 1. This provided the titled product.

Step G: Preparation of 1-(3-Chlorophenyl)-4-[1-(4-cyano-3-(trifluoromethoxy)benzyl)-5-imidazolylmethyl]-2-piperazinone dihydrochloride The titled compound was prepared from the product of Step F (264 mg, 0.89 mmol) and the product of Step J of Example 1 using the procedure described in Step K of Example 1. Purification by silica gel column chromatography (50–65% acetoneldichloro methane) and conversion to the dihydrochloride salt using excess ethereal HCl solution gave the titled product as a white powder.

FAB ms (m+1) 490.1.

Anal. Calc. for C₂₃H19ClF₃N₅O₂•2.00 HCl•1.0 H₂O: C, 47.56; H, 3.99; N, 12.06.

Found: C, 47.58; H. 4.02; N, 11.91.

4-[1-(4-Cyano-3-(trifluoromethoxy)benzyl)-5-imidazolylmethyl]-1-3-(trifluoromethoxy)phenyl]-2-piperazinone dihydrochloride Step A: Preparation of 1-[3-(trifluoromethoxy)phenyl]-2-piperazinone hydrochloride The titled compound was prepared from 3-(trifluoromethoxy)aniline using the procedures described in Steps F–J of Example 1.

Step B: Preparation of 4-[1-(4-cyano3-(trifluoromethoxy) benzyl)-5-imidazolylmethyl]-1-[3-(trifluoromethoxy) phenyl]-2-piperazinone dihydrochloride The titled compound was prepared from the product of Step A and the product of Step F of Example 9 using the procedure described in Step K of Example 1. Purification by silica gel column chromatography (50–65% acetone/dichloro methane) and conversion to the dihydrochloride salt using excess ethereal HCl solution gave the titled product as a white powder.

FAB ms (m+1) 540.2.

Anal. Calc. for C₂₄H₁₉F₆N₅O₂•2.00 HCl•1.15 H₂O•0.50 CH₂Cl₂: C, 44.61; H, 3.71; N, 10.62.

Found: C, 44.63; H, 3.70; N, 10.56.

EXAMPLE 11

1-(3-Chlorophenyl)-4-[1-(4-cyano-3-fluorobenzyl)-5-imidazolylmethyl]-2-piperazinone dihydrochloride Step A: Preparation of 4-cyano-3-fluorotoluene To a degassed solution of 4-bromo3-fluorotoluene (50.0 g, 264 mmol) in 500 mL of DMF was added Zn(CN)₂ (18.6 g, 159 mmol) and Pd(PPh₃)₄ (6.1 g, 5.3 mmol). The reaction was stirred at 80° C. for 6 hours, then cooled to room temperature. The solution was poured into EtOAc, washed with water, sat. aq. NaHCO₃, and brine, then dried (Na₂SO₄), filtered, and concentrated in vacuo to provide the crude product. Purification by silica gel chromatography (0–5% EtOAc/hexane) provided the titled product.

Step B: Preparation of 4-cyano-3-fluorobenzylbromide

To a solution of the product from Step A (22.2 g, 165 mmol) in 220 mL of carbontetrachloride was added N-bromosuccinimide (29.2 g, 164 mmol) and benzoylperoxide (1.1 g). The reaction was heated to reflux for 30 minutes, then cooled to room temperature. The solution was concentrated in vacuo to one-third the original volume, poured into EtOAc, washed with water, sat. aq. NaHCO₃, and brine, then dried (Na₂SO₄), filtered, and concentrated in vacuo to provide the crude product. Analysis by 1H NMR indicated only partial conversion, so the crude material was resubjected to the same reaction conditions for 2.5 hours, using 18 g (102 mmol) of N-bromosuccinimide. After workup, the crude material was purified by silica gel chromatography (0–10% EtOAc/hexane) to provide the desired product.

Step C: Preparation of 1-(4-cyano-3-fluorobenzyl)-5-(acetoxymethyl)-imidazole hydrobromide A solution of the product from Step B (20.67 g, 96.14 mmol) and the product from Step B of Example 1 (36.72 g, 96.14 mmol) in 250 mL of EtOAc was stirred at 60 °C. for 20 hours, during which a white precipitate formed. The reaction was cooled to room temperature and filtered to provide the solid imidazolium bromide salt. The filtrate was concentrated in vacuo to a volume of 100 mL, reheated at 60° C. for two hours, cooled to room temperature, and filtered again. The filtrate was concentrated in vacuo to a volume 40 mL, reheated at 60° C. for another two hours, cooled to room temperature, and concentrated in vacuo to provide a pale yellow solid. All of the solid material was combined, dissolved in 300 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step D: Preparation of 1-(4-cyano-3-fluorobenzyl)-5-(hydroxymethyl)imidazole

To a solution of the product from Step C (31.87 g, 89.77 mmol) in 300 mL of 2:1 THF/water at 0° C. was added lithium hydroxide monohydrate (7.53 g, 179 mmol). After two hours, the reaction was concentrated in vacuo to a 100 mL volume, stored at 0° C. for 30 minutes, then filtered and washed with 700 mL of cold water to provide a brown solid. This material was dried in vacuo next to P₂O, to provide the titled product as a pale brown powder which was sufficiently pure for use in the next step without further purification.

Step E: Preparation of 1-(4-cyano-3-fluorobenzyl)-5-imidazolecarboxaldehyde

To a solution of the alcohol from Step D (2.31 g, 10.0 mmol) in 20 mL of DMSO at 0° C. was added triethylamine (5.6 mL, 40 mmol), then SO₃-pyridine complex (3.89 g, 25 mmol). After 30 minutes, the reaction was poured into EtOAc, washed with water and brine, dried ($Na_2SO_4$), filtered, and concentrated in vacuo to provide the aldehyde as a pale yellow powder which was sufficiently pure for use in the next step without further purification.

Step F: Preparation of 1-(3-Chlorophenyl)-4-[1-(4-cyano-3-fluorobenzyl)-5-imidazolylmethyl]-2-piperazinone dihydrochloride The titled compound was prepared from the product of Step A and the product of Step F of Example 9 using the procedure described in Step K of Example 1. Purification by silica gel column chromatography (50–60% acetone/dichloromethane) and conversion to the dihydrochloride salt using excess ethereal HCl solution gave the titled product as a white powder.

FAB ms (m+1) 424.2.

Anal. Calc. for $C_{22}H_{19}ClFN_5O_2$•2.00 HCl•1.15 $H_2O$: C, 51.05; H, 4.54; N, 13.53.

Found: C, 51.08; H, 4.62; N, 13.44.

EXAMPLE 12

1-(3-Chlorophenyl)-4-[1-(4-cyano-3-(methylthio) benzyl)-5-imidazolylmethyl]-2-piperazinone dihydrochloride To a solution of the Example 11 product (52 mg, 0.12 mmol) in 1 mL of DMF was added sodium thiomethoxide (17 mg, 0.24 mmol). After ca. 16 hours, the reaction was diluted with EtOAc and extracted with saturated $NaHCO_3$ solution and brine, dried over sodium sulfate, filtered, and concentrated in vacuo. Purification by silica gel preparative thin-layer chromatography (2×0.5 mm, 10% $CHCl_3$/methanol) and conversion to the dihydrochloride salt using excess ethereal HCl solution gave the titled product as a white powder.

HPLC: 100% purity at 220 nm; retention time=8.24 min; 5–95% gradient: acetonitrile/0.1% TFA-water over 15 min.

Anal. Calc. for $C_{23}H_{22}ClN_5OS$•2.00 HCl•0.15 $H_2O$•0.30 $CH_2Cl_2$: C, 50.59; H, 4.54; N, 12.66.

Found: C, 51.21; H, 5.08; N, 11.88.

EXAMPLE 13

1-(3-Chlorophenyl)-4-[1-(4-cyano-3-(phenoxy) benzyl)-5-imidazolylmethyl]-2-piperazinone dihydrochloride To a solution of the Example 11 product (50 mg, 0.12 mmol) in 1 mL of DMSO was added phenol (33 mg, 0.35 mmol), followed by cesium carbonate (114 mg, 0.35 mmol). After ca. 16 hours, the reaction was diluted with EtOAc and extracted with water and brine, dried over sodium sulfate, filtered, and concentrated in vacuo. Purification by silica gel preparative thin-layer chromatography (2×0.5 mm, 90:10:1 $CHCl_3$/methanol/$NH_4OH$) and conversion to the dihydrochloride salt using excess ethereal HCl solution gave the titled product as a white powder.

FAB ms (m+1) 498.2.

Anal. Calc. for $C_{28}H_{24}ClN_5O_2$•2.00 HCl•0.50 $H_2O$•0.10 $CH_2Cl_2$: C, 57.35; H, 4.66; N, 11.90.

Found: C, 57.37; H, 4.67; N, 11.13.

EXAMPLE 14

The following compounds were also prepared by procedures analogous to those described in Examples 1–13:

1-(3-Chlorophenyl)-4-[1-(2-fluoro-4-cyanobenzyl)-1H-imidazol-5-ylmethyl]piperazin-2-one dihydrochloride Anal. $C_{22}H_{19}ClFN_5O$ 2 HCl 1$H_2O$
Calc: C, 51.33; H, 4.50; N, 13.60
Found: C, 51.41; H, 4.49; N, 13.16

4-[1-(4-Cyanobenzyl)-1H-imidazol-5-ylmethyl]-1-(3-methylthiophenyl)piperazin-2-one dihydrochloride
Anal. $C_{23}H_{23}N_5OS$ 2.5 HCl
Calc: C, 54.33; H, 5.06; N, 13.77
Found: C, 54.37; H, 4.75; N, 13.13

4-[1-(4-Cyanobenzyl)-1H-imidazol-5-ylmethyl]-1-(3,5-dichlorophenyl)piperazin-2-one dihydrochloride
Anal. $C_{22}H_{19}Cl_2N_5O$ 2.55 HCl 1 $H_2O$
Calc: C, 47.92; H, 4.31; N, 12.70
Found: C, 47.95; H, 4.31; N, 12.65

1-(3-Chlorophenyl)-4-{[1-(4-cyanophenyl)-1-ethyl]-1H-imidazol-5-ylmethyl}piperazin-2-one dihydrochloride
Anal. $C_{23}H_{22}ClN_5O$ 2 HCl 1.3 $H_2O$
Calc: C, 53.51; H, 5.19; N, 13.57
Found: C, 53.59; H, 5.39; N, 13.44

1-(3-Chloro-4-fluorophenyl)-4-[1-(4-cyanobenzyl)-1H-imidazol-5-ylmethyl]piperazin-2-one dihydrochoride
Anal. $C_{22}H_{19}ClFN_5O$ 2 HCl
Calc: C, 53.19; H, 4.26; N, 14.10
Found: C, 52.84; H, 4.37; N, 13.76

4-[1-(4-Cyanobenzyl)-1H-imidazol-5-ylmethyl]-1-(3,5-dimethylphenyl)piperazin-2-one dihydrochloride
Anal. $C_{24}H_{25}N_5O$ 2 HCl 0.1 $H_2O$
Calc: C, 60.79; H, 5.78; N, 14.77
Found: C, 60.79; H, 6.32; N, 14.34

(S)-5-Benzyl-4-[3-(4-cyanobenzyl)-1-imidazol-5-yl)prop-1-yl]-1-phenyl-2-piperazinone dihydrochloride
FAB mns nile 490 (m+1).
Anal. $C_{31}H_{31}N_5O$ 2 HCl 1.45 $H_2O$
Calc: C, 63.25; H, 6.15; N, 11.90
Found: C, 63.22; H, 5.98; N,11.64

1-(3-Chlorophenyl)-4-[1-(4-nitrobenzyl)-1H-imidazol-5-ylmethyl]piperazin-2- one
Anal. $C_{21}H_{20}ClN_5O_3$ 0.15 $H_2O$
Calc: C, 58.85; H, 4.77; N, 16.34
Found: C, 58.82; H, 4.55; N, 16.35

4-[1-(4-Cyanobenzyl)-1H-imidazol-5-ylmethyl]-1-(3,5-difluorophenyl)piperazin-2-one dihydrochloride
Anal. $C_{22}H_{19}F_2N_5O$ 2 HCl 0.25 EtOAc
Calc: C, 54.98; H, 4.61; N, 13.94
Found: C, 54.72; H, 4.68; N, 13.80

4-[1-(4-Cyanobenzyl)-1H-imidazol-5-ylmethyl]-1-(3,4-difluorophenyl)piperazin-2-one ditrifluoroacetic acid salt
Anal. $C_{22}H_{19}F_2N_5O$ 2 TFA 0.35 $H_2O$
Calc: C, 48.66; H, 3.41; N, 10.91
Found: C, 48.29; H, 3.44; N, 11.30

EXAMPLE 15

In vitro inhibition of ras farnesyl transferase

Transferase Assays. Isoprenyl-protein transferase activity assays are carried out at 30° C. unless noted otherwise. A typical reaction contains (in a final volume of 50 mL): [$^3$H]farnesyl diphosphate, Ras protein, 50 mM HEPES, pH 7.5, 5 mM $MgCl_2$, 5 mM dithiothreitol, 10 mM $ZnCl_2$, 0.1% polyethyleneglycol (PEG) (15,000–20,000 mw) and isoprenyl-protein transferase. The FPTase employed in the assay is prepared by recombinant expression as described in Omer, C. A., Kral, A. M., Diehl, R. E., Prendergast, G. C., Powers, S., Allen, C. M., Gibbs, J. B. and Kohl, N. E. (1993) Biochemistry 32:5167–5176. After thermally pre-equilibrating the assay mixture in the absence of enzyme, reactions are initiated by the addition of isoprenyl-protein transferase and stopped at timed intervals (typically 15 min) by the addition of 1M HCl in ethanol (1 mL). The quenched reactions are allowed to stand for 15 m (to complete the precipitation process). After adding 2 mL of 100% ethanol, the reactions are vacuum-filtered through Whatman GF/C filters. Filters are washed four times with 2 mL aliquots of 100% ethanol, mixed with scintillation fluid (10 mL) and then counted in a Beckman LS3801 scintillation counter.

For inhibition studies, assays are run as described above, except inhibitors are prepared as concentrated solutions in 100% dimethyl sulfoxide and then diluted 20-fold into the enzyme assay mixture. Substrate concentrations for inhibitor $IC_{50}$ determinations are as follows: FTase, 650 nM Ras—CVLS (SEQ. ID. NO.: 1), 100 nM farnesyl diphosphate.

The compounds of the instant invention described in the above Examples 1–14 were tested for inhibitory activity against human FPTase by the assay described above and were found to have $IC_{50}$ of $\leq 50$ mM.

EXAMPLE 16
Modified in vitro GGTase inhibition assay

The modified geranylgeranyl-protein transferase inhibition assay is carried out at room temperature. A typical reaction contains (in a final volume of 50 mL): [$^3$H] geranylgeranyl diphosphate, biotinylated Ras peptide, 50 mM HEPES, pH 7.5, a modulating anion (for example 10 mM glycerophosphate or 5 mM ATP), 5 mM $MgCl_2$, 10 mM $ZnCl_2$, 0.1% PEG (15,000–20,000 mw), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 2). Reactions are initiated by the addition of GGTase and stopped at timed intervals (typically 15 min) by the addition of 200 mL of a 3 mg/mL suspension of streptavidin SPA beads (Scintillation Proximity Assay beads, Amersham) in 0.2M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. $IC_{50}$ values are determined with Ras peptide near $K_M$ concentrations. Enzyme and substrate concentrations for inhibitor $IC_{50}$ determinations are as follows: 75 pM G;GTase-I, 1.6 mM Ras peptide, 100 nM geranylgeranyl diphosphate.

EXAMPLE 17
Cell-basedin vitro ras farnesylation assay

The cell line used in this assay is a v-ras line derived from either Rat1 or N1H$_3$T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labeled in 3 ml methionine-free DMEM supplemented with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin12 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immuno-precipitated with the ras-specific monoclonal antibody Y13-259 (Furth, M. E. et al, *J. Virol.* 43:294–304, (1982)). Following a 2 hour antibody incubation at 4° C., 200 ml of a 25% suspension of protein A-Sepharose coated with rabbit anti rat IgG is added for 45 min. The immuno-precipitates are washed four times with IP buffer (20 nM HEPES, pH 7.5/1 mM EDTA/1% Triton X-100.0.5% deoxycholate/ 0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

EXAMPLE 18
Cell-basedin vitro growth inhibition assay

To determine the biological consequences of FPTase inhibition, the effect of the compounds of the instant invention on the anchorage-independent growth of RatL cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

EXAMPLE 19
Construction of SEAP reporter plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, CA). The plasmid pCMV-RE-AKI was constructed by Deborah Jones (Merck) and contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of *E. coli* DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Kienow DNA Polymerase I. The SEAP DNA fragment was blunt end ligated into the pCMV-RE-AKI vector and the ligation products were transformed into DH$_5$-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Alternative Construction of SEAP reporter plasmid, pDSE101

The SEAP reporter plasmid, pDSE101 is also constructed by ligating a restriction fragment containing the SEAP coding sequence into the plasmid pCMV-RE-AKI. The SEAP gene is derived from plasmid pGEM7zf(-)/SEAP.

The plasmid pDSE101 was constructed as follows: A restriction fragment containing part of the SEAP gene coding sequence was cut out of the plasmid pGEM7zf(-)/SEAP using the restriction enzymes Apa I and KpnI. The ends of the linear DNA fragments were chewed back with the Kienow fragment of *E. coli* DNA Polymerase I. The "blunt ended" DNA containing the truncated SEAP gene was isolated by electrophoresing the digest in an agarose gel and cutting out the 1910 base pair fragment. This 1910 base pair fragment was ligated into the plasmid pCMV-RE-AKI which had been cut with Bgl-II and filled in with *E. coli* KLenow fragment DNA polymerase. Recombinant plasmids were screened for insert orientation and sequenced through the ligated junctions. The plasmid pCMV-RE-AKI is derived from plasmid pCMVIE-AKI-DHFR (Whang , Y., Silberklang, M., Morgan, A., Munshi, S., Lenny, A. B., Ellis, R. W., and Kieff, E. (1987) J. Virol., 61, 1796–1807) by removing an EcoRl fragment containing the DHFR and Neomycin markers. Five copies of the fos promoter serum response element were inserted as described previously (Jones, R. E., Defeo-Jones, D., Mcvoy, E. M., Vuocolo, G. A., Wegrzyn, R. J., Haskell, K. M. and Oliff, A. (1991) Oncogene, 6, 745–751) to create plasmid pCMV-RE-AKI.

The plasmid pGEM7zf(-)/SEAP was constructed as folows. The SEAP gene was PCRed, in two segments from a human placenta cDNA library (Clontech) using the following oligos.

Sense strand N-terminal SEAP: 5' GAGAGGGAAT-TCGGGCCCTTCCTGCAT GCTGCTGCTGCTGCT-GCTGGGC 3' (SEQ.ID.NO.:3)

Antisense strand N-terminal SEAP: 5' GAGAGAGCTC-GAGGTTAACCCGGGT GCGCGGCGTCGGTGGT 3' (SEQ.ID.NO.:4)

Sense strand C-terminal SEAP: 5' GAGAGAGTCTA-GAGTTAACCCGTGGTCC CCGCGTTGCTTCCT 3' (SEQ.ID.NO.:5)

Antisense strand C-terminal SEAP: 5' GAAGAG-GAAGCTTGGTACCGCCACTG GGCTGTAGGTGGTG-GCT 3' (SEQ.ID.NO.:6)

The N-terminal oligos (SEQ.ID.NO.: 4 and SEQ.ID.NO.: 5) were used to generate a 1560 bp N-terminal PCR product that contained EcoRI and HpaI restriction sites at the ends. The Antisense N-terminal oligo (SEQ.ID.NO.: 4) introduces an internal translation STOP codon within the SEAP gene along with the HpaI site. The C-terminal oligos (SEQ.ID.NO.: 5 and SEQ.ID.NO.: 6) were used to amplify a 412 bp C-terminal PCR product containing HpaI and HindIII restriction sites. The sense strand C-terminal oligo (SEQ.ID.NO.: 5) introduces the internal STOP codon as well as the Hpal site. Next, the N-terminal amplicon was digested with EcoRI and HpaI while the C-terminal amplicon was digested with plpaI and HindIII. The two fragments comprising each end of the SEAP gene were isolated by electrophoresing the digest in an agarose gel and isolating the 1560 and 412 base pair fragments. These two fragments were then coligated into the vector GEM7zf(-) (Promega) which had been restriction digested with EcoRI and HindIII and isolated on an agarose gel. The resulting clone, pGEM7zf(-)/SEAP contains the coding sequence for the SEAP gene from amino acids.

Construction of a constitutively expressing SEAP plasmid pCMV-SEAP

An expression plasmid constitutively expressing the SEAP protein was treated by placing the sequence encoding a truncated SEAP gene downstream of the cytomegalovirus (CMV) IE-1 promoter. The expression plasmid also includes the CMV intron A region 5' to the SEAP gene as well as the 3' untranslated region of the bovine growth hormone gene 3' to the SEAP gene.

The plasmid pCMVIE-AKI-DHFR (Whang et al, 1987) containing the CMV immediate early promoter was cut with EcoRI generating two fragments. The vector fragment was isolated by agarose electrophoresis and relegated. The resulting plasmid is named pCMV-AKI. Next, the cytomegalovirus intron A nucleotide sequence was inserted downstream of the CMV IE1 promoter in pCNW-AKI. The intron A sequence was isolated from a genomic clone bank and subcloned into pBR$^{322}$ to generate plasmid pl6T-286. The intron A sequence was mutated at nucleotide 1856 (nucleotide numbering as in Chapman, B. S., Thayer, R. M., Vincent, K. A. and Haigwood, N. L., Nuc.Acids Res. 19, 3979–3986) to remove a SacI restriction site using site directed mutagenesis. The mutated intron A sequence was PCRed from the plasmid p16T-287 using the following oligos.

Sense strand: 5' GGCAGAGCTCTCGTTTAGTGAAC-CGTCAG 3' (SEQ.ID.NO.: 7)

Antisense strand: 5' GAGAGATCTCAAGGACGGT-GACTGCAG 3' (SEQ.ID.NO.: 8)

These two oligos generate a 991 base pair fragment with a SacI site incorporated by the sense oligo and a Bgl-II fragment incorporated by the antisense oligo. The PCR fragment is trimmed with SacI and Bgl-II and isolated on an agarose gel. The vector pCMV-AKI is cut with SacI and Bgl-II and the larger vector fragment isolated by agarose gel electrophoresis. The two gel isolated fragments are ligated at their respective SacI and Bgl-II sites to create plasmid pCMV-AKI-InA.

The DNA sequence encoding the truncated SEAP gene is inserted into the pCMV-AKI-InA plasmid at the Bgl-II site of the vector. The SEAP gene is cut out of plasmid pGEM7zf (-)/SEAP (described above) using EcoRI and HindIII. The fragment is filled in with Klenow DNA polymerase and the 1970 base pair fragment isolated from the vector fragment by agarose gel electrophoresis. The pCMV-AKI-InA vector is prepared by digesting with Bgl-II and filling in the ends with Klenow DNA polymerase. The final construct is generated by blunt end ligating the SEAP fragment into the pCMV-AKI-InA vector. Transformants were screened for the proper insert and then mapped for restriction fragment orientation. Properly oriented recombinant constructs were sequenced across the cloning junctions to verify the correct sequence. The resulting plasmid, named pCMV-SEAP, contains a modified SEAP sequence downstream of the cytomegalovirus immediately early promoter IE-1 and intron A sequence and upstream of the bovine growth hormone poly-A sequence. The plasmid expresses SEAP in a constitutive manner when transfected into mammalian cells.

Cloning of a Myristylated viral-H-ras expression plasmid

A DNA fragment containing viral-H-ras can be PCRed from plasmid "H-1" (Ellis R. et al. J. Virol. 36, 408, 1980) or "HB-11 (deposited in the ATCC under Budapest Treaty on Aug. 27, 1997, and designated ATCC 209,218) using the following oligos.

Sense strand:
5'TCTCCTCGAGGCCACCATGGGGAGTAG-CAAGAGCAAGCCTAA GGACCCCAGCCAGCGCCG-GATGACAGAATACAAGCTTGTGGTG G 3'. (SEQ.ID.NO.: 9)

Antisense:

5'CACATCTAGATCAGGACAGCACAGACT-TGCAGC 3'. (SEQ.ID.NO.: 10)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site. To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3' end. The XhoI-XbaI fragment can be ligated into the mammalian expression plasmid pCI (Promega) cut with XhoI and XbaI. This results in a plasmid in which the recombinant myr-viral-H-ras gene is constitutively transcribed from the CMV promoter of the pCI vector.

Cloning of a viral-H-ras-CVLL expression plasmid

A viral-H-ras clone with a C-terminal sequence encoding the amino acids CVLL can be cloned from the plasmid "H-1" (Ellis R. et al. J. Virol. 36, 408, 1980) or "HB-11 (deposited in the ATCC under Budapest Treaty on Aug. 27, 1997, and designated ATCC 209,218) by PCR using the following oligos.

Sense strand:

5'TCTCCTCGAGGCCACCATGACAGAATACAAG CTTGTGGTGG-3' (SEQ.ID.NO.: 11)

Antisense strand:

5'CACTCTAGACTGGTGTCAGAGCAGCACACAC TTGCAGC-3' (SEQ.ID.NO.: 12)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid in which the mutated viral-H-ras-CVLL gene is constitutively transcribed from the CMV promoter of the pCI vector.

Cloning of c-H-ras-Leu61 expression plasmid

The human c-H-ras gene can be PCRed from a human cerebral cortex cDNA library (Clontech) using the following oligonucleotide primers.

Sense strand:

5'-GAGAGAATTCGCCACCATGACGGAATATAAG CTGGTGG-3' (SEQ.ID.NO.: 13)

Antisense strand:

5'-GAGAGTCGACGCGTCAGGAGAGCACACAC TTGC-3' (SEQ.ID.NO.: 14)

The primers will amplify a c-H-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-H-ras fragment can be ligated ligated into an EcoRI —Sal I cut mutagenesis vector pAlter-1 (Promega). Mutation of glutamine-61 to a leucine can be accomplished using the manufacturer's protocols and the following oligonucleotide:

5'-CCGCCGGCCTGGAGGAGTACAG-3' (SEQ.ID.NO.: 15)

After selection and sequencing for the correct nucleotide substitution, the mutated c-H-ras-Leu6l can be excised from the pAlter-1 vector, using EcoRI and Sal I, and be directly ligated into the vector pCI (Promega) which has been digested with EcoRI and Sal I. The new recombinant plasmid will constitutively transcribe c-H-ras-Leu61 from the CMV promoter of the pCI vector.

Cloning of a c-N-ras-Val-12 expression plasmid

The human c-N-ras gene can be PCRed from a human cerebral cortex cDNA library (Clontech) using the following oligonucleotide primers.

Sense strand:

5'-GAGAGAATTCGCCACCATGACTGAGTAC AAACTGGTGG-3' (SEQ.ID.NO.: 16)

Antisense strand:

5'-GAGAGTCGACTTGTTACATCACCACACATGGC-3' (SEQ.ID.NO.: 17)

The primers will amplify a c—N-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c—N-ras fragment can be ligated into an EcoRI-Sal I cut mutagenesis vector pAlter-I (Promega). Mutation of glycine-12 to a valine can be accomplished using the manufacturer's protocols and the following oligonucleotide:

5'-GTTGGAGCAGTTGGTGTTGGG-3' (SEQ.ID.NO.: 18)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid will constitutively transcribe c-N-ras-Val-12 from the CMV promoter of the pCI vector.

Cloning of a c-K-ras-Val-12 expression plasmid

The human c-K-ras gene can be PCRed from a human cerebral cortex cDNA library (Clontech) using the following oligonucleotide primers.

Sense strand:

5'-GAGAGGTACCGCCACCATGACTGAATATAAA CTTGTGG-3' (SEQ.ID.NO.: 19)

Antisense strand:

5'-CTCTGTCGACGTATTTACATAATTACACACTT TGTC-3' (SEQ.ID.NO.: 20)

The primers will amplify a c-K-ras encoding DNA fragment with the primers contributing an optimized 'Kozak' translation start sequence, a KpnI site at the N-terminus and a Sal I stite at the C-terminal end- After trimming the ends of the PCR product with Kpn I and Sal I, the c-K-ras fragment can be ligated into a KpnI-Sal I cut mutagenesis vector pAlter-1 (Promega). Mutation of cysteine-12 to a valine can be accomplished using the manufacturer's protocols and the following oligonucleotide:

5'-GTAGTTGGAGCTGTTGGCGTAGGC-3' (SEQ.ID.NO.: 21)

After selection and sequencing for the correct nucleotide substitution, the mutated c-K-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K-ras-Val-12 from the CMV promoter of the pCI vector.

SEAP assay

Human $C_{33}A$ cells (human epitheial carcenoma—ATTC collection) are seeded in 10 cm tissue culture plates in DMEM+10% fetal calf serum+1X Pen/Strep+1X glutamine+1X NEAA. Cells are grown at 37° C. in a 5% $CO_2$ atmosphere until they reach 50–80% of confluency.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. For 10 cm plates 600 ml of $CaCl_2$-DNA solution is added dropwise while vortexing to 600 ml of 2X HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. # 31053-028)+0.5% charcoal stripped calf serum+1X (Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+1X (Pen/Strep, Glutamine and NEAA). Transfected cells are plated in a 96 well microtiter plate (100 ml/well) to which drug, diluted in media, has already been added in a volume of 100 ml. The final volume per well is 200 ml with each drug concentration repeated in triplicate over a range of half-log steps.

Incubation of cells and drugs is for 36 hrs at 37° C. under $CO_2$. At the end of the incubation period, cells are examined microscopically for evidence of cell distress. Next, 100 ml of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 ml media is combined with 200 ml of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

| DNA-$CaPO_4$ precipitate for 10 cm. plate of cells | |
|---|---|
| Ras expression plasmid (1 mg/ml) | 10 ml |
| DSE-SEAP Plasmid (1 mg/ml) | 2 ml |
| Sheared Calf Thymus DNA (1 mg/ml) | 8 ml |
| 2M $CaCl_2$ | 74 ml |
| $dH_2O$ | 506 ml |
| 2X HBS Buffer | |
| 280 mM NaCl | |
| 10 mM KCl | |
| 1.5 mM $Na_2HPO_4$ $2H_2O$ | |
| 12 mM dextrose | |
| 50 mM HEPES | |
| Final pH = 7.05 | |
| Luminesence Buffer (26 ml) | |
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |
| Assay Buffer | |
| Add 0.05M $Na_2CO_3$ to 0.05M $NaHCO_3$ to obtain pH 9.5. Make 1 mM in $MgCl_2$ | |

EXAMPLE 20

The processing assays employed are modifications of that described by DeClue et al [Cancer Research 51, 712–717, 1991].

K4B-Ras processing inhibition assay

PSN-1 (human pancreatic carcinoma) or viral-K4 B-ras-transformed Rat1 cells are used for analysis of protein processing. Subconfluent cells in 100 mm dishes are fed with 3.5 ml of media (methionine-free RPMI supplemented with 2% fetal bovine serum or cysteine-freetmethionine-free DMEM supplemented with 0.035 ml of 200 mM glutamine (Gibco), 2% fetal bovine serum, respectively) containing the desired concentration of test compound, lovastatin or solvent alone. Cells treated with lovastatin (5–10 $\mu$M), a compound that blocks Ras processing in cells by inhibiting a rate-limiting step in the isoprenoid biosynthetic pathway, serve as a positive control. Test compounds are prepared as 1000' concentrated solutions in DMSO to yield a final solvent concentration of 0.1%. Following incubation at 37° C. for two hours 204 $\mu$Ci/ml [$^{35}$S]Pro-Mix (Amersham, cell labeling grade) is added.

After introducing the label amino acid mixture, the cells are incubated at 37° C. for an additional period of time (typically 6 to 24 hours). The media is then removed and the cells are washed once with cold PBS. The cells are scraped into 1 ml of cold PBS, collected by centrifugation (10,000×g for 10 sec at room temperature), and lysed by vortexing in 1 ml of lysis buffer (1% Nonidet P-40, 20 mM HEPES, pH 7.5, 150 mM NaCl, 1 mM EDTA, 0.5% deoxycholate, 0.1% SDS, 1 mM DTT, 10 $\mu$g/ml AEBSF, 10 $\mu$g/ml aprotinin, 2 $\mu$g/ml leupeptin and 2 $\mu$g/ml antipain). The lysate is then centrifuged at 15,000×g for 10 min at 4° C. and the supernatant saved.

For immunoprecipitation of Ki4B-Ras, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 8 $\mu$g of the pan Ras monoclonal antibody, Y13-259, added. The protein/antibody mixture is incubated on ice at 40° C. for 24 hours. The immune complex is collected on pansorbin (Calbiochem) coated with rabbit antiserum to rat IgG (Cappel) by tumbling at 40° C. for 45 minutes. The pellet is washed 3 times with 1 ml of lysis buffer lacking DTT and protease inhibitors and resuspended in 100 ml elution buffer (10 mM Tris pH 7.4, 1% SDS). The Ras is eluted from the beads by heating at 95° C. for 5 minutes, after which the beads are pelleted by brief centrifugation (15,000×g for 30 sec. at room temperature).

The supernatant is added to 1 ml of Dilution Buffer 0.1% Triton X-100, 5 mM EDTA, 50 mM NaCl, 10 mM Tris pH 7.4 ) with 2 mg Kirsten-ras specific monoclonal antibody, c-K-ras Ab-1 (Calbiochem). The second protein/antibody mixture is incubated on ice at 4° C. for 1–2 hours. The immune complex is collected on pansorbin (Calbiochem) coated with rabbit antiserum to rat IgG (Cappel) by tumbling at 40° C. for 45 minutes. The pellet is washed 3 times with 1 ml of lysis buffer lacking DTT and protease inhibitors and resuspended in Laemmli sample buffer. The Ras is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100 ), and the Ras visualized by fluorography.

EXAMPLE 21

Rap1 processing inhibition assay

Protocol A:

Cells are labeled, incubated and lysed as described in Example 20.

For immunoprecipitation of Rap1, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 2 gg of the Rap1 antibody, Rap1/Erev1

(121) (Santa Cruz Biotech), is added. The protein/antibody mixture is incubated on ice at 4° C. for 1 hour. The immune complex is collected on pansorbin (Calbiochem) by tumbling at 4° C. for 45 minutes. The pellet is washed 3 times with 1 ml of lysis buffer lacking DTT and protease inhibitors and resuspended in 100 ml elution buffer (10 mM Tris pH 7.4, 1% SDS). The Rap1 is eluted from the beads by heating at 95° C. for 5 minutes, after which the beads are pelleted by brief centrifugation (15,000×g for 30 sec. at room temperature).

The supernatant is added to 1 ml of Dilution Buffer (0.1% Triton X-100, 5 mM EDTA, 50 mM NaCl, 10 mM Tris pH 7.4 ) with 2 mg Rap1 antibody, Rap1/Krev1 (121) (Santa Cruz Biotech). The second protein/antibody mixture is incubated on ice at 4° C. for 1–2 hours. The immune complex is collected on pansorbin (Calbiochem) by tumbling at 4° C. for 45 minutes. The pellet is washed 3 times with 1 ml of lysis buffer lacking DTT and protease inhibitors and resuspended in Laemmli sample buffer. The Rap1 is eluted from the beads by heating at 95° C. for 5 minutes, after which the beads are pelleted by brief centrifugation. The supernatant is subjected to SDSPAGE on a 12% acrylamide gel (bis-acrylamide:acrylamide, 1:100 ), and the Rap1 visualized by fluorography.

Protocol B:

PSN-1 cells are passaged every 3–4 days in 10 cm plates, splitting near-confluent plates 1:20 and 1:40. The day before the assay is set up, $5 \times 10^6$ cells are plated on 15 cm plates to ensure the same stage of confluency in each assay. The media for these cells is RPM1 1640 (Gibco), with 15% fetal bovine serum and 1× Pen/Strep antibiotic mix.

The day of the assay, cells are collected from the 15 cm plates by tiypsinization and diluted to 400,000 cells/ml in media. 0.5 ml of these diluted cells are added to each well of 24-well plates, for a final cell number of 200,000 per well. The cells are then grown at 37° C. overnight.

The compounds to be assayed are diluted in DMSO in ½-log dilutions. The range of final concentrations to be assayed is generally 0.1–100 μM. Four concentrations per compound is typical. The compounds are diluted so that each concentration is 1000× of the final concentration (i.e., for a 10 μM data point, a 10 mM stock of the compound is needed).

2 μL of each 1000× compound stock is diluted into 1 ml media to produce a 2X stock of compound. A vehicle control solution (2 μL DMSO to 1 ml media), is utilized. 0.5 ml of the 2X stocks of compound are added to the cells.

After 24 hours, the media is aspirated from the assay plates. Each well is rinsed with 1 ml PBS, and the PBS is aspirated. 180 μL SDS-PAGE sample buffer (Novex) containing 5% 2 -mercapto-ethanol is added to each well. The plates are heated to 100° C. for 5 minutes using a heat block containing an adapter for assay plates. The plates are placed on ice. After 10 minutes, 20 μL of an RNAse/DNase mix is added per well. This mix is 1 mg/ml DNaseI (Worthington Enzymes), 0.25 mg/ml Rnase A (Worthington Enzymes), 0.5M Tris-HCl pH 8.0 and 50 mM $MgCl_2$. The plate is left on ice for 10 minutes. Samples are then either loaded on the gel, or stored at −70° C.

Each assay plate (usually 3 compounds, each in 4-point titrations, plus controls) requires on e15-well 14% Novex gel. 25 μl of each sample is loaded onto the gel. The gel is run at 15 mA for about 3.5 hours. It is important to run the gel far enough so that there will be adequate separation between 21 kd (Rap1) and 29 kd (Rab6).

The gels are then transferred to Novex pre-cut PVDF membranes for 1.5 hours at 30V (constant voltage). Immediately after transferring, the membranes are blocked overnight in 20 ml Western blocking buffer (2% nonfat dry milk in Western wash buffer (PBS+0.1% Tween-20). If blocked over the weekend, 0.02% sodium azide is added. The membranes are blocked at 4° C. with slow rocking.

The blocking solution is discarded and 20 ml fresh blocking solution containing the anti Rap1a antibody (Santa Cruz Biochemical SC1482) at 1:1000 (diluted in Western blocking buffer) and the anti Rab6 antibody (Santa Cruz Biochemical SC310) at 1:5000 (diluted in Western blocking buffer) are added. The membranes are incubated at room temperature for 1 hour with mild rocking. The blocking solution is then discarded and the membrane is washed 3 times with Western wash buffer for 15 minutes per wash. 20 ml blocking solution containing 1:1000 (diluted in Western blocking buffer) each of two alkaline phosphatase conjugated antibodies (Alkaline phosphatase conjugated Anti-goat IgG and Alkaline phosphatase conjugated anti-rabbit IgG [Santa Cruz Biochemical] is then added. The membrane is incubated for one hour and washed 3× as above.

About 2 ml per gel of the Amersham ECF detection reagent is placed on an overhead transparency (ECF) and the PVDF membranes are placed face-down onto the detection reagent. This is incubated for one minute, then the membrane is placed onto a fresh transparency sheet.

The developed transparency sheet is scanned on a phosphorimager and the Rap1a Minimum Inhibitory Concentration is determined from the lowest concentration of compound that produces a detectable Rap1a Western signal. The Rap1a antibody used recognizes only unprenylated/unprocessed Rap1a, so that the presence of a detectable Rap1a Western signal is indicative of inhibition of Rap1a prenylation.

EXAMPLE 22

In vivo tumor growth inhibition assay (nude mouse) In vivo efficacy as an inhibitor of the growth of cancer cells may be confirmed by several protocols well known in the art. Examples of such in vivo efficacy studies are described by N. E. Kohl et al. (Nature Medicine, 1:792–797 (1995 )) and N. E. Kohl et al. (Proc. Nat. Acad. Sci. U.S.A., 91:9141–9145 (1994 )).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound which inhibits farnesyl-protein transferase which is:

1-(3 -Trifluoromethoxyphenyl)-4-[1-(4-cyanobenzyl) imidazolylmethyl]-2 -piperazinone 1-(2,5-Dimethylphenyl)-4-[1-(4-cyanobenzyl) imidazolylmethyl]-2-piperazinone 1-(3-Methylphenyl)-4-[1-(4-yanobenzyl) imidazolylmethyl]-2-piperazinone 1-(3-Iodophenyl)4-[1-(4-cyanobenzyl) imidazolylmethyl]-2-piperazinone 1-(3-Chlorophenyl)-4-[1-(3-methoxy-4-cyanobenzyl) imidazolylmethyl]-2-piperazinone 1-(3-Trifluoromethoxyphenyl)-4-[1-( 3-methoxy-4-cyanobenzyl)imidazolylmethyl]-2-piperazinone (R)-5-[(Benzyloxy)methyl]-1-(3-chlorophenyl)4-[1-(4-cyanobenzyl)-imidazolylmethyl]-2-piperazinone 1-(3-Chlorophenyl)-4-[1-(2-fluoro-4-cyanobenzyl)-1H-imidazol-5-ylmethyl]piperazin-2-one 4-[1-(4-Cyanobenzyl)-1H-imidazol-5-ylmethyl]-1-(3-methylthiophenyl)piperazin-2-one 4-[1-(4-Cyanobenzyl)-1H-imidazol-5-ylmethyl]-1-(3,5-dichlorophenyl)piperazin-2-one 1-(3-Chlorophenyl)-4-{[1-(4-cyanophenyl) 1-ethyl1-1H-imidazol-5-ylmethyl}piperazin-2-one 1-(3-Chloro-4-fluorophenyl)-4-[1-(4-cyanobenzyl)-1H-imidazol-5-ylmethyl]piperazin-2-one 4-[1-(4-Cyanobenzyl)-1H-imidazol-5-ylmethyl]-1-(3,5-dimethylphenyl)piperazin-2-one (S)-5-Benzyl-4-[3-(4-cyanobenzyl-1-imidazol-5-yl)prop-1-phenyl-2-piperazinone 1-(3-Chlorophenyl)4-[1-(4nitrobenzyl)-1H-imidazol-5-ylmethyl]piperazin-2-one 4-[1-(4-Cyanobenzyl)-1H-imidazol-5-ylmethyl]-1-(3,5-difluorophenyl)piperazin-2-one or 4-[1-(4-Cyanobenzyl)-1H-imidazol-5-ylmethyl]-1-(3,4-difluorophenyl)piperazin-2-one or a pharmaceutically acceptable salt or optical isomer thereof.

2. A pharmaceutical composition comprising a pharmaceutical carrier, and dispersed therein, a therapeutically effective amount of a compound of claim 1.

3. A method for inhibiting farnesyl-protein transferase and geranylgeranyl-protein transferase type I which comprises administering to a mammal in need thereof a therapeutically effective amount of a compound of claim 1.

4. A method for treating cancer which comprises administering to a mammal in need thereof a therapeutically effective amount of a compound of claim 1.

5. A method according to claim 4 wherein the cancer is characterized by a mutated K4B-Ras protein.

6. A method for treating neurofibromin benign proliferative disorder which comprises administering to a mammal in need thereof a therapeutically effective amount of a compound of claim 1.

7. A method for treating blindness related to retinal vascularization which comprises administering to a mammal in need thereof a therapeutically effective amount of a compound of claim 1.

8. A method for treating infections from hepatitis delta and related viruses which comprises administering to a mammal in need thereof a therapeutically effective amount of a compound of claim 1.

9. A method for preventing restenosis which comprises administering to a mammal in need thereof a therapeutically effective amount of a compound of claim 1.

10. A method for treating polycystic kidney disease which comprises administering to a mammal in need thereof a therapeutically effective amount of a compound of claim 1.

11. A pharmaceutical composition made by combining the compound of claim 1 and a pharmaceutically acceptable carrier.

12. A process for making a pharmaceutical composition comprising combining a compound of claim 1 and a pharmaceutically acceptable carrier.

* * * * *